US011052147B2

(12) United States Patent
Sediq et al.

(10) Patent No.: US 11,052,147 B2
(45) Date of Patent: Jul. 6, 2021

(54) STABLE VIRUS-CONTAINING COMPOSITION

(71) Applicants: Janssen Vaccines & Prevention B.V., Leiden (NL); Bavarian Nordic A/S, Kvistgaard (DK)

(72) Inventors: Ahmad Shakeb Sediq, Basel (CH); Wouter Frank Tonnis, Berlin (DE); Martinus Anne Hobbe Capelle, Sassenheim (NL)

(73) Assignee: JANSSEN VACCINES & PREVENTION B.V.

(*) Notice: Subject to any disclaimer, the term of this patent is extended or adjusted under 35 U.S.C. 154(b) by 0 days.

(21) Appl. No.: 16/612,561

(22) PCT Filed: May 15, 2018

(86) PCT No.: PCT/IB2018/053390
§ 371 (c)(1),
(2) Date: Nov. 11, 2019

(87) PCT Pub. No.: WO2018/211419
PCT Pub. Date: Nov. 22, 2018

(65) Prior Publication Data
US 2020/0197512 A1    Jun. 25, 2020

(30) Foreign Application Priority Data

May 15, 2017   (EP) ..................................... 17171105
Oct. 30, 2017  (EP) ..................................... 17199139

(51) Int. Cl.
| A61K 39/00 | (2006.01) |
| A61K 39/12 | (2006.01) |
| C12N 15/86 | (2006.01) |
| C12N 7/00 | (2006.01) |
| A61K 39/275 | (2006.01) |
| A61K 39/285 | (2006.01) |
| A61P 31/04 | (2006.01) |
| A61K 47/20 | (2006.01) |

(52) U.S. Cl.
CPC ............ *A61K 39/285* (2013.01); *A61K 47/20* (2013.01); *A61P 31/04* (2018.01)

(58) Field of Classification Search
CPC ...... A61P 37/04; A61P 35/00; A61K 2300/00; A61K 2039/5256; C12N 2710/24143
See application file for complete search history.

(56) References Cited

U.S. PATENT DOCUMENTS

| 3,919,044 A | 11/1975 | Melnick et al. |
| 5,879,924 A | 3/1999 | Foster |
| 6,761,893 B2 | 7/2004 | Chaplin |
| 6,913,752 B2 | 7/2005 | Chaplin |
| 7,410,644 B2 | 8/2008 | Schlom |
| 7,456,009 B2 | 11/2008 | Evans |
| 7,914,979 B2 | 3/2011 | Chen |
| 9,492,533 B2 | 11/2016 | Friedman |
| 9,623,059 B2 | 4/2017 | Mohr |
| 2005/0118192 A1 | 6/2005 | Boursnell |
| 2005/0186225 A1 | 8/2005 | Evans et al. |
| 2007/0161085 A1 | 7/2007 | Trager |
| 2014/0056942 A1 | 2/2014 | Qiao et al. |
| 2016/0136262 A1 | 5/2016 | Meijberg |
| 2016/0176932 A1 | 6/2016 | Langedijk |

FOREIGN PATENT DOCUMENTS

| WO | 9010459 A1 | 9/1990 |
| WO | 9205263 A1 | 4/1992 |
| WO | 9421807 A2 | 9/1994 |
| WO | 9509241 A2 | 4/1995 |
| WO | 9804705 A1 | 2/1998 |
| WO | 9903885 A1 | 1/1999 |
| WO | 200168820 A1 | 9/2001 |
| WO | 2002042480 A2 | 5/2002 |
| WO | 2003054175 A1 | 7/2003 |
| WO | 2004022729 A1 | 3/2004 |
| WO | 2004111082 A2 | 12/2004 |
| WO | 2005007840 A1 | 1/2005 |
| WO | 2005/028634 A2 | 3/2005 |
| WO | WO2005028634 | * 3/2005 |
| WO | 2007077256 A1 | 7/2007 |
| WO | 2007121894 A2 | 11/2007 |
| WO | 2007147528 A1 | 12/2007 |
| WO | 2008045346 A2 | 4/2008 |
| WO | 2008129058 A1 | 10/2008 |
| WO | 2008138533 A1 | 11/2008 |
| WO | 2009004016 A1 | 1/2009 |

(Continued)

OTHER PUBLICATIONS

Int'l Search Report and Written Opinion dated Jul. 6, 2018 in Inn Application No. PCT/IB2018/053390.
Apte et al, "Effect of Buffers and Stabilizers on Vaccine Stability and Efficacy," Development of Vaccines, vol. 8, pp. 399-414 (2011).
Rapp et al, "Protection of Measles Virus by Sulfate Ions Against Thermal Inactivation," Journal of Bacteriology, vol. 90, No. 1, pp. 132-135 (1965).
Paneque-Quevedo, "Inorganic Compounds as Vaccine Adjuvants," Biotecnologia Aplicado, vol. 30, No. 4, pp. 250-256 (2013).
Aghi et al, "Oncolytic viral therapies—the clinical experience," Oncogene, vol. 24, pp. 7802-7816 (2005).
Boukamp et al, "Normal Keratinization in a Spontaneously Immortalized Aneuploid Human Keratinocyte Cell Line," Journal of Cell Biology, vol. 106, No. 3, pp. 761-771 (1988).

(Continued)

*Primary Examiner* — Barry A Chestnut
(74) *Attorney, Agent, or Firm* — Ice Miller LLP

(57) ABSTRACT

Described herein are compositions and pharmaceutical compositions including poxviruses, in particular vaccinia virus such as modified vaccinia Ankara (MVA) virus, a sulfate salt at a concentration between about 5 mM and 300 mM and a buffer, wherein the composition has a pH of between about 6.0 and 8.5. Also described are methods for stabilizing a poxvirus composition by preparing said viral formulation.

20 Claims, 9 Drawing Sheets

(56) References Cited

FOREIGN PATENT DOCUMENTS

Figure 1:
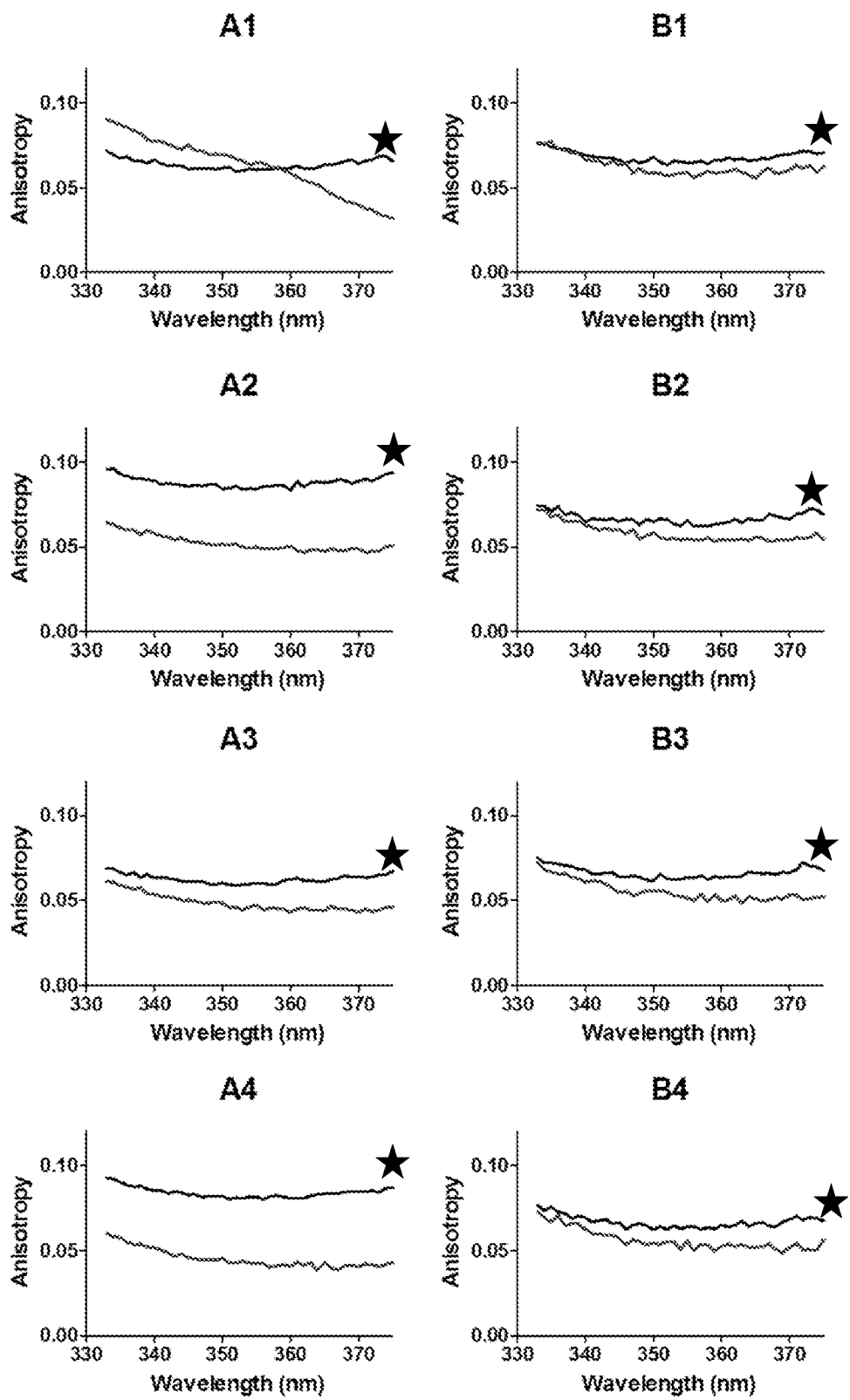

| WO | 2009079796 A1 | 7/2009 |
| --- | --- | --- |
| WO | 2009100521 A1 | 8/2009 |
| WO | 2010/130753 A1 | 11/2010 |
| WO | 2010149743 A2 | 12/2010 |
| WO | 2010149745 A1 | 12/2010 |
| WO | 2011015656 A2 | 2/2011 |
| WO | 2012010280 A1 | 1/2012 |
| WO | 2012048817 A2 | 4/2012 |
| WO | 2012158613 A1 | 11/2012 |
| WO | 2013007772 A1 | 1/2013 |
| WO | 2013/177172 A2 | 11/2013 |
| WO | 2014019718 A1 | 2/2014 |
| WO | 2014029702 A1 | 2/2014 |
| WO | 2014053571 A1 | 4/2014 |
| WO | 2015/057548 A1 | 4/2015 |
| WO | 2015175340 A1 | 11/2015 |
| WO | 2016/034678 A2 | 3/2016 |
| WO | 2016/087457 A1 | 6/2016 |
| WO | 2016202828 A1 | 12/2016 |

OTHER PUBLICATIONS

Carroll et al, "Host Range and Cytopathogenicity of the Highly Attenuated MVA Strain of Vaccinia Virus: Propagation and Generation of Recombinant Viruses in a Nonhuman Mammalian Cell Line", Virology, vol. 238, pp. 198-211 (1997).

Evans et al, "Development of Stable Liquid Formulations for Adenovirus-Based Vaccines," Journal of Pharmaceutical Sciences, vol. 93, No. 10, pp. 2458-2475 (Oct. 2004).

Flood et al, "Development of a Freeze-Dried, Heat-Stable Influenza Subunit Vaccine Formulation," PLoS One, vol. 11, No. 11, p. e0164692 (Nov. 2016).

Forrester et al, "Construction and Properties of a Mutant of Herpes Simplex Virus Type 1 with Glycoprotein H Coding Sequences Deleted," Journal of Virology, vol. 66, No. 1, pp. 341-348 (Jan. 1992).

Johnson et al, "The Fusion Glycoproteins of Human Respiratory Syncytial Virus of Subgroups A and B: Sequence Conservation Provides a Structural Basis for Antigenic Relatedness," Journal of General Virology, vol. 69, pp. 2623-2628 (1988).

Leon et al, "The EB66® cell line as a valuable cell substrate for MVA-based vaccines production," Vaccine, vol. 34, pp. 5878-5885 (2016).

Rexroad et al, "Lyophilization and the Thermostability of Vaccines," vol. 1, No. 2, pp. 91-104 (2002).

Schweneker et al, "Recombinant Modified Vaccinia Virus Ankara Generating Ebola Virus-Like Particles," Journal of Virology, vol. 91, No. 11, p. e00343-17 (Jun. 2017).

Toda et al, "Herpes Simplex as an in Situ Cancer Vaccine for the Induction of Specific Anti-Tumor Immunity," Human Gene Therapy, vol. 10, pp. 385-393 (Feb. 1999).

Vasco et al, "Critical Evaluation of Nanoparticle Tracking Analysis (NTA) by NanoSight for the Measurement of Nanoparticles and Protein Aggregates," Pharmaceutical Research, vol. 27, No. 5, pp. 796-810 (May 2010).

Wallis et al, "Stabilization of Enveloped Viruses by Dimethyl Sulfoxide," Journal of Virology, vol. 2, No. 9, pp. 353-954 (Sep. 1968).

Welliver, "Introduction," The Journal of Pediatrics, vol. 143, p. S112 (2003).

Intl Search Report and Written Opinion dated Jul. 3, 2018 in Intl Application No. PCT/EP2018/062506.

* cited by examiner

STABLE VIRUS-CONTAINING COMPOSITION

STATEMENT OF GOVERNMENT SUPPORT

This invention was made with government support under contract HHSO100201500008C, awarded by the Department of Health and Human Services of the United States of America; Office of the Assistant for Preparedness and Response; Biomedical Advanced Research and Development Authority. The government of the United States of America has certain rights in the invention.

CROSS-REFERENCE TO RELATED APPLICATIONS

This application is a national stage application under 35 U.S.C. § 371 of PCT/IB18/53390, filed Nov. 15, 2018, which claims priority under 35 U.S.C. § 119(b) to European Patent Application No. 17199139.1, filed on Oct. 30, 2017, and European Patent Application No. 17171105.4, filed on May 15, 2017, the entire contents of each of which are incorporated herein by reference in their entirety.

FIELD OF THE INVENTION

The invention relates to the field of poxvirus containing compositions and related pharmaceutical products suitable for storage. Preferred compositions as disclosed herein are compositions comprising poxviruses such as vaccinia virus or modified vaccinia Ankara (MVA) virus, a sulfate salt and a buffer such as a phosphate or a Tris-buffer for use in long-term storage. The compositions may in particular be used as vaccine or therapeutic against various pathogens or diseases.

BACKGROUND OF THE INVENTION

Poxviruses such as vaccinia virus and modified vaccinia Ankara (MVA) virus are used as prophylactic vaccines against smallpox. Additionally, recombinant vaccinia virus and MVA are currently used in many clinical studies for prophylactic or therapeutic vaccinations against many pathogens or targets including cancer. Like other live or inactivated virus vaccines prophylactic or therapeutic poxvirus pharmaceuticals need to be stored before they are applied to the recipients or patients and thus need to be stored over days, weeks or several months up to several years without losing their potency. Since the envelope of the poxvirus is involved in cell entry and a prerequisite for replication or for expression of recombinant antigens to stimulate the desired immune response in a subject, a decrease in viral titer goes hand in hand with changes in infectivity and thus the effectivity of the product.

Usually enveloped viruses demonstrate even greater lability during storage than those lacking envelopes, suggesting that the lipid bilayer is a major factor of virus instability. Vaccinia viruses are not only of exceptionally big size (about 200 to 300 nm) but also their envelopes are even more complex than the envelope from other viruses. In addition to the intracellular surrounded membrane, poxviruses acquire an additional membrane when they detach from the surface. Stabilizing the vaccinia virus is thus even more challenging than for other enveloped viruses. For instance, WO 2016/087457 discloses several tested liquid formulations with various additives having a negative influence on the stability of the MVA. It therefore requires a tailored approach to find a robust formulation for poxviruses ensuring stability over a wide range of conditions.

WO 03/053463 and WO 2014/053571 disclose freeze-dried formulations comprising MVA. However, freeze-dried processes are more time-consuming and require additives to preserve the biological activity of the virus during the drying process to avoid loss of activity. Furthermore, a reconstitution step is needed prior to administration, which complicates the administration procedure.

Accordingly, there remains a need in the art for developing stable poxviral vaccine formulations for pharmaceutical application allowing industrial application and storage over a prolonged period of time without affecting the biological activity of the product. More particularly, viral titer loss and/or formation of by-products with potential increased toxicity or altered immunogenicity should be limited to a minimum. The vaccine should also be protected against shear forces during application and clinical use and be protected against elevated temperature dependent on various climate situations in particular upon transport or to avoid loss of potency due to improper observation or interruption of the cold chain. Furthermore, there is a need to retain activity after one or more freeze and thaw cycles during manufacturing of the product, storage and transportation. Since extracellular vesicles containing virus encoded membrane proteins are a by-product of recombinant poxvirus production, the formulation of poxviruses (e.g., vaccinia virus or MVA) is even further complicated and requires a tailored approach considering many variables affecting viral infectivity. These and other objects of the invention will be described in further detail in connection with the detailed description of the invention.

BRIEF SUMMARY OF THE INVENTION

To meet these and other needs, described herein are compositions comprising poxviruses with improved thermal stability and improved stability against agitation stress as compared to previously disclosed formulations. The poxviruses contained in said compositions retain their potency and infectivity. This was achieved by the addition of sulfate salts, preferably sodium sulfate at a concentration between about 5 mM and 300 mM to the poxvirus in a buffer having a pH ranging between about 6.0 and 8.5. These compositions improve upon conventional compositions known in the art by showing less aggregation and conformational changes of the virus, less pH change upon storage and/or less change in turbidity when stored for example at room temperature, at −20° C. storage temperature or following accelerated stress. Specifically, the present invention is expected to fulfil target product profile characteristics of shelf life at 25° C. for weeks or months or at 2° C. to 8° C. for a longer period of time and outside of frozen conditions. The present invention also provides shelf life below 0° C. specifically at −20° C. for weeks or months or longer period of time.

The present invention therefore provides a composition comprising a) a poxvirus; b) a buffer; and c) a sulfate salt at a concentration between about 5 mM and 300 mM, wherein said composition has a pH of between about 6.0 and 8.5.

In some embodiments, the invention relates to a pharmaceutical composition comprising a) a poxvirus; b) a buffer; and c) a sulfate salt at a concentration between about 5 mM and 300 mM, wherein said formulation has a pH of between about 6.0 and 8.5.

In some embodiments, the composition or pharmaceutical composition is suitable for administration by injection, e.g., by intramuscular, subcutaneous, intravenous, or intranasal application. For example, the pharmaceutical composition can be used for treatment or preventing against a pathogen or cancer.

In some embodiments, the invention relates to a method of stabilizing a poxvirus composition comprising preparing a composition comprising a) a poxvirus; b) a buffer; and c) a sulfate salt at a concentration between about 5 mM and 300 mM, wherein said composition has a pH of between about 6.0 and 8.5.

In some embodiments the invention relates to a method of stabilizing a poxvirus composition comprising a step of preparing a composition comprising a poxvirus; b) a buffer; and c) a sulfate salt at a concentration between about 5 mM and 300 mM, wherein said composition has a pH of between about 6.0 and 8.5 and storing said composition at a temperature ranging between 2 degrees centigrade and 8 degrees centigrade.

In some embodiments, the invention relates to a method of stabilizing a poxvirus composition comprising a step of adding a sulfate salt at a concentration between about 5 mM and 300 mM to a poxvirus composition.

BRIEF DESCRIPTION OF THE DRAWINGS

The accompanying drawings, which are incorporated in and constitute a part of this specification, illustrate several embodiments of the invention and together with the description, serve to explain the principles of the invention. It should be understood that the invention is not limited to the precise embodiments shown in the drawings.

FIG. 1: Anisotropy results obtained using Fluoromax 4 for the different formulations without $Na_2SO_4$ (A1-A4, 10 mM Tris pH 7.5, 8.0, 8.5 and 9.0) and with 100 mM $Na_2SO_4$ (B1-B4, 10 mM Tris pH 7.5, 8.0, 8.5 and 9.0, 100 mM $Na_2SO_4$). The black lines (indicated with *) show the scans obtained before accelerated stress (1 week 25° C.), and the grey lines after the stress.

FIG. 2: From top down: changes in pH, emission peak shift, changes in emission intensities, changes in Z-average diameter and changes in polydispersity index (PDI) after applied accelerated stress (1 week 25° C.) are shown for different formulations without $Na_2SO_4$ (A1-A4; 10 mM Tris pH 7.5, 8.0, 8.5 and 9.0) and with 100 mM $Na_2SO_4$ (B1-B4; 10 mM Tris pH 7.5, 8.0, 8.5 and 9.0, 100 mM $Na_2SO_4$).

FIG. 3: From left to right, each column of graphs shows the changes in turbidity, Z-average diameter and polydispersity index (PDI) after applied accelerated stress (1 day 37° C.). The different groups of formulations are arranged in the vertical plane, namely from top down: formulations containing no salts (formulations A1-A4), formulations containing 100 mM $Na_2SO_4$ (formulations B1-B4), formulations containing 100 mM $CaCl_2$ (formulations C1-C4), formulations containing 100 mM $MgSO_4$ (formulations D1-D4), formulations containing 100 mM $MgCl_2$ (formulations E1-E4) and formulations containing 140 mM NaCl (formulations F1-F4). The formulations are fully described in Example 3.

FIG. 4: From left to right, each column of graphs shows the changes in turbidity, Z-average diameter and polydispersity index (PDI) after applied accelerated stress (1 day 37° C.). The different groups of formulations are arranged in the vertical plane, namely from top down: formulations containing no salts (formulations A1-A4), formulations containing 100 mM $Na_2SO_4$ (formulations B1-B4), formulations containing 100 mM $MgCl_2$ (formulations C1-C4), and formulations containing 100 mM NaCl (formulations D1-D4). The formulations are fully described in Example 4.

FIG. 5 Anisotropy. Fluorescence emission and 90 degrees Light Scattering results obtained using Fluoromax 4 for four different formulations (Control A, 1, Control B and 3). The blackline indicated with * represents the scans at T0, whereas the line without the * represents the scan after applying stress in the form of a 3 months storage at 5° C. The formulations are fully described in Example 6.

FIG. 6: Anisotropy, Fluorescence emission and 90 degrees Light Scattering results obtained using Fluoromax 4 for four different formulations (Control A, 1. Control B and 3). The blackline indicated with * represents the scans at T0, whereas the line without the * represents the scan after applying stress in the form of a 3 months storage at −20° C. The formulations are fully described in Example 6.

FIG. 7: Anisotropy. Fluorescence emission and 90 degrees Light Scattering results obtained using Fluoromax 4 for four different formulations (Control A, 1, Control B and 3). The blackline indicated with * represents the scans at T0, whereas the line without the * represents the scan after applying accelerated stress in the form of 20 freeze-thaw cycles. The formulations are fully described in Example 6.

FIG. 8: Anisotropy, Fluorescence emission and 90 degrees Light Scattering results obtained using Fluoromax 4 for five formulations (Control A, 1, Control B, 3 and 7). The blackline indicated with * represents the scans at T0, whereas the line without the * represents the scan after applying accelerated stress in the form of agitation for 1 day (24 h) at 200 rpm. The formulations are fully described in Example 6.

FIG. 9: From left to right, each column of graphs shows the turbidity. Z-average diameter and polydispersity index (PDI). From top to bottom, the graphs show the values after preparation (T0), after 3 months at 5° C. (3M5C), after 3 months at −20° C. (3M-20° C.), after 20 freeze-thaw cycles (20FT) and after 1 day agitation (AG). Formulations are arranged on the x-axis of these graphs (Control A, 1, Control B, 3 and 7). The formulations are fully described in Example 6.

DETAILED DESCRIPTION OF THE INVENTION

The specification discloses one or more embodiments that incorporate the features of this invention. The disclosed embodiments merely exemplify the invention. The scope of the invention is not limited to the disclosed embodiments.

Various publications, articles, patent applications and patents are cited or described in the background and throughout the specification; each of these references is herein incorporated by reference in its entirety. To the extent the material incorporated by reference contradicts or is inconsistent with this specification, the specification will supersede any such material. Discussion of documents, acts, materials, devices, articles or the like which has been included in the present specification is for the purpose of providing context to the invention. Such discussion is not an admission that any or all of these matters form part of the prior art with respect to any invention disclosed or claimed.

It is to be understood that this invention is not limited to the particular methodology, protocols and reagents described herein as these may vary. It is also to be understood that the terminology used herein is for the purpose of describing particular embodiments only, and is not intended to limit the scope of the present invention. Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a", "an", and "the" include plural reference unless the context clearly dictates otherwise. Thus, for example, reference to "a nucleic acid" includes one or more nucleic acid sequences and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. It must also be noted that unless otherwise stated, any numerical value, such as a concentration or a concentration range described herein, are to be understood as being modified in all instances by the term "about." Through the specification the term "about" with respect to any quantity or concentration is contemplated to include that quantity. For example, "about 5 mM" is contemplated herein to include 5 mM as well as values understood to be approximately 5 mM with respect to the entity described. As used herein, the use of a numerical range expressly includes all possible subranges, all individual numerical values within that range, including integers within such ranges and fractions of the values unless the context clearly indicates otherwise. Likewise the term "about" preceding any numerical value or range used herein in the context of the invention can be deleted and be replaced by the numerical value or range without the term "about" though less preferred.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or when used herein with the term "having". Any of the aforementioned terms (comprising, containing, including, having), whenever used herein in the context of an aspect or embodiment of the present invention may be substituted with the term "consisting of" or "consisting essentially of" though less preferred.

When used herein "consisting of" excludes any element, step, or ingredient not specified in the claim element. When used herein, "consisting essentially of" does not exclude materials or steps that do not materially affect the basic and novel characteristics of the claim.

The term "aggregation" as used herein refers to the process wherein two or more proteins or viruses accumulate and/or clump together. Aggregation may occur for intact, native proteins as well as for degraded proteins. Often protein aggregation is caused by the exposure of hydrophobic groups of proteins which then accumulate. Virus aggregation may occur due to the modification of proteins expressed on the viral envelope.

The term "nucleic acid", "nucleotide sequence", "nucleic acid sequence" and "polynucleotide" can be used interchangeably and refers to RNA or DNA that is linear or branched, single or double stranded, or a hybrid thereof. The term also encompasses RNA/DNA hybrids. The polynucleotides can be obtained by chemical synthesis or derived from a microorganism. The term "exogenous" nucleic acid sequences when used in connection with a recombinant virus means a foreign nucleic acid sequence, a nucleic acid sequence not contained in the non-recombinant virus used for generating the recombinant virus or inserted into the virus genome while generating the recombinant virus.

The terms "pharmaceutical", "pharmaceutical composition" and "medicament" are used interchangeably herein referring to a substance and/or a combination of substances being used for the prevention or treatment of a disease.

"Pharmaceutically acceptable" means that the carrier, additive, antibiotic, preservative, adjuvant, diluent, stabilizers, or excipient, at the dosages and concentrations employed, will not cause any unwanted or harmful effect(s) in the subject(s) to which they are administered.

The terms "subject" and "patient" are used interchangeably. As used herein, a subject is typically a mammal, such as a non-primate (e.g., cows, pigs, horses, cats, dogs, rats, etc.) or a primate (e.g., monkey and human), and in some preferred embodiments a human.

According to the present invention, "virus" means viruses, virus particles, viral vectors and viral vaccines. The terms can all be used interchangeably. This term includes wild-type viruses, recombinant and non-recombinant viruses, live viruses and live-attenuated viruses.

The practice of this invention will employ, unless otherwise indicated, conventional techniques of analytics, immunology, molecular biology, microbiology, cell biology, and recombinant DNA, which are within the skill of the art. See e.g. Sambrook. Fritsch and Maniatis. Molecular Cloning: A Laboratory Manual, $2^{nd}$ edition, 1989; Current Protocols in Molecular Biology, Ausubel F M, et al., eds, 1987; the series Methods in Enzymology (Academic Press, Inc.); PCR2: A Practical Approach, MacPherson M J, Hams B D, Taylor G R, eds, 1995; Antibodies: A Laboratory Manual, Harlow and Lane, eds, 1988.

Throughout the specification, except where stated otherwise, values of physical parameters such as pH are those measured at 25° C.

The present invention is directed to a composition of a poxvirus comprising a sulfate salt at a concentration between about 5 mM and 300 mM and a buffer having a pH ranging between about 6.0 and 8.5.

The term "composition" refers to a formulation containing an active pharmaceutical or biological ingredient e.g., a recombinant MVA, along with one or more additional components. The term "composition" and "formulation" is used interchangeably with the terms "pharmaceutical composition". "vaccine composition", "vaccine", and "vaccine formulation" herein.

In certain embodiments, the formulation, composition, pharmaceutical composition, vaccine composition, vaccine, or vaccine formulation is a stable or stabilized composition.

By "stable", "stabilized", "stability" or "stabilizing", which can all be used interchangeable, it is understood that the poxvirus contained in the composition of the present invention essentially retains its physical stability, identity, integrity, and/or chemical stability, identity, integrity, particle morphology and/or biological activity or potency upon storage required for shelf life of a pharmaceutical composition.

Various analytical techniques for measuring the stability are known to the skilled person and said characteristics which determine the stability may be determined by at least one of the methods selected from the group consisting of Intrinsic Fluorescence, Anisotropy, Dynamic Light Scattering, pH measurement, Turbidity measurements at 350 nm and 90 degrees Light Scattering as described in more detail in the examples. Stability can be measured at a selected temperature and other storage conditions for a selected time period.

Methods to determine particle morphology are well known to the skilled person. For example particle morphology can be determined using transmission electron microscopy and immunoelectron microscopy (immune-EM) as for example described in Schweneker et al., Recombinant modified vaccinia virus Ankara generating Ebola virus-like particles. J. of Virology 22 Mar. 2017. Alternative methods to determine particle morphology is the Nanoparticle Tracking Analysis (NTA) described for example in Vasco et al. (2010), Critical Evaluation of Nanoparticle Tracking Analysis (NTA) by NanoSight for the Measurement of Nanoparticles and Protein Aggregates. Pharmaceutical Research. 27: 796-810. Nanoparticle tracking analysis (NTA) is a method for the direct and real-time visualization and analysis of particle size distribution and aggregation in liquids. Based on a laser illuminated microscopic technique, Brownian motion of nanoparticles is analyzed in real-time by a charge-couple device (CCD) camera, each particle being simultaneously but separately visualized and tracked by a dedicated particle tracking image-analysis program. The ability of NTA to measure simultaneously particle size and particle scattering intensity allows heterogeneous particle mixtures to be resolved and particle concentration to be estimated directly.

The term "potency" or "infectivity", as used herein refers to the activity of the poxvirus (e.g., vaccinia virus or MVA) expressed as infectious units (InfU) usually given as InfU/mL or Tissue culture Infectious Dose 50 ($TCID_{50}$) given as $TCID_{50}$/mL. Both terms "potency" and "infectivity" can be used interchangeably in the present invention. The potency of a poxvirus such as MVA can be determined using various methods known to the skilled person such as for example by Fluorescence Activated Cell Sorter (FACS) assay or a Tissue Culture Infectious Dose 50 ($TCID_{50}$) assay. An exemplary FACS assay and $TCID_{50}$ assay as used in the present invention are described in the examples.

As used herein, the term "shelf life" means the time that a product remains active and/or stable according to the product characteristics under specified storage conditions (e.g., storage at 2° C. to 8° C.) for use as a human medication. Shelf lives correspond to the time points for which the lower limit or upper limit of a given specification is exceeded.

In certain embodiments, the composition of any of the embodiments of the present invention is further defined as having an infectivity of at least 50%, 60%, 79%, 80% or 90% of the starting infectivity (at day 0) when stored for six months at 4° C.

In certain embodiments, the composition of any of the embodiments of the present invention is further defined as having an infectivity of at least 50%, 60%, 79%, 80% or 90% of the starting infectivity (at day 0) when stored for three months at 25° C.

In certain embodiments, the composition of any of the embodiments of the present invention is further defined as having an infectivity of at least 50%, 60%, 79%, 80% or 90% of the starting infectivity (at day 0) when stored for three, preferably six months at −20° C.

In certain embodiments, the composition of any of the embodiments of the present invention has a decrease of infectivity of not more than 50%, 40%, 30%, 20%, 10% or 5% of the starting infectivity (at day 0) when stored for six months at 4° C.

In certain embodiments, the composition of any of the embodiments of the present invention has a decrease of infectivity of not more than 50%, 40%, 30%, 20%, 10% or 5% of the starting infectivity (at day 0) when stored for three months at 25° C.

In certain embodiments, the composition of any of the embodiments of the present invention has a decrease of infectivity of not more than 50%/o, 40%, 30%, 20% 10% or 5% of the starting infectivity (at day 0) when stored for three months, preferably six months at −20° C.

According to particular embodiments, the composition of the present invention is stable when the overall loss of virus titer at 25° C. (+/−5° C.) for 3 week (preferably three months, six months or at least one year) is less than 0.5 $\log_{10}$ InfU/mL or $TCID_{50}$/mL, preferably less than 0.4 $\log_{10}$ InfU/mL or $TCID_{50}$/mL, more preferably less than 0.3 $\log_{10}$ InfU/mL or $TCID_{50}$/mL.

The "overall loss of virus titer" according to the present invention is defined as the cumulative loss in virus titer measured during storage of the composition at the indicated temperature n (e.g., at 37° C.) and time t (e.g. for 1 week) given as $\log_{10}$ $TCID_{50}$/mL. Alternative, it can be given as $\log_{10}$ InfU/mL. The overall loss of virus titer is given as x log 10 (e.g., as 0.5 $\log_{10}$ at 37° C. for 1 week).

In various embodiments, accelerated stress can be measured using accelerated stability studies performed at elevated temperature to shorten the stability evaluation of compositions e.g., 37° C. for 1 week. Such accelerated stability studies allow predicting the stability at higher temperatures without having to wait for the real data.

In preferred embodiments of the present invention, the loss in virus titer during storage is less than 0.4 logic InfU/mL or $TCID_{50}$/mL at 5° C.+/−3° C. for at least 3 months, preferably less than 0.3 $\log_{10}$ InfU/mL or $TCID_{50}$/mL at 5° C.+/−3° C. for at least 3 months, more preferably less than 0.2 $\log_{10}$ InfU/mL or $TCID_{50}$/mL at 5° C.+/−3° C. for at least 3 months.

In preferred embodiments of the present invention, the loss in virus titer during storage is less than 0.4 $\log_{10}$ InfU/mL or $TCID_{50}$/mL at −20° C.+/−3° C. for at least 3 months, preferably less than 0.3 $\log_{10}$ InfU/mL or $TCID_{50}$/mL at −20° C.+/−3° C. for at least 3 months, more preferably less than 0.2 logic InfU/mL or $TCID_{50}$/mL at −20° C.+/−3° C. for at least 3 months.

In preferred embodiments of the present invention, the loss in virus titer during storage is less than 0.4 $\log_{10}$ InfU/mL or $TCID_{50}$/mL at −50° C.+/−3° C. for at least 3 months, preferably less than 0.3 $\log_{10}$ InfU/mL or $TCID_{50}$/mL at −50° C.+/−3° C. for at least 3 months, more preferably less than 0.2 $\log_{10}$ InfU/mL or $TCID_{50}$/mL at −50° C.+/−3° C. for at least 3 months.

In preferred embodiments of the present invention, the loss in virus titer during storage is less than 0.4 $\log_{10}$ InfU/mL or $TCID_{50}$/mL at −80° C.+/−3° C. for at least 3 months, preferably less than 0.3 $\log_{10}$ InfU/mL or TCID$_{50}$/mL at −80° C.+/−3° C. for at least 3 months, more preferably less than 0.2 $\log_{10}$ InfU/mL or TCID$_{50}$/mL at −80° C.+/−3° C. for at least 3 months.

The assay to determine poxvirus titer is for example described in Kaufmann and Kabelitz (2002), Methods in Microbiology Volume 32: Immunology of Infection, Academic Press. ISBN 0125215320. The titer from the assay is reported as Plaque Forming Unit per milliliter (PFU/mL). The FACS assay and TCID$_{50}$ assay as used for the present invention is described in the examples and can alternatively be used in addition to any other suitable method.

According to preferred embodiments, the composition of the present invention is an aqueous composition. In certain embodiments, the composition is suitable for storage at room temperature (e.g., at ambient temperature), between about −20° C., and 25° C., between about −20° C., and 4° C., between about 2° C., and 25° C., or between about 2° C. and 8° C. The composition of any of the embodiments can be liquid or liquid frozen. The composition of the present invention are amenable for prolonged storage between about −20° C., and 25° C., between about −20° C., and 4° C., between about 2° C., and 25° C., or between about 2° C., and 8° C. for more than 3 months, 6 months, 9 months 12 months, 24 months or more at each specified temperature range. In preferred embodiments of the present invention, the composition comprising the poxvirus are amenable for prolonged storage at 2° C. to 8° C. for more than 6 months, 9 months, 12 months, 24 months or more. As used herein, "room temperature" or ambient "temperature" is a temperature of 25° C.+/−3° C.

Poxviruses of the Invention

Poxvirus according to the present invention refers to any of the genera of poxviruses capable of infecting humans (e.g., orthopoxviruses, avipoxviruses, parapoxviruses, yatapoxviruses, and molluscipoxviruses).

In various embodiments, the poxvirus is selected from the group of orthopoxviruses and avipoxviruses.

In various embodiments of the present disclosure, the poxvirus is preferably an avipoxvirus. Avipoxviruses include canarypox virus (CNPV) and fowlpox virus (FWPV).

In various embodiments of the present disclosure, the poxvirus is preferably an orthopoxvirus (OPV). Orthopoxviruses according to the present invention can include, but are not limited to, smallpox virus (also known as variola virus), vaccinia virus, cowpox virus, and monkeypox virus.

In various embodiments of the present invention, the poxvirus is a vaccinia virus or a FWPV.

Numerous FWPV strains are suitable for the present invention. They are known to the skilled person and are described for example as FPV in WO 2016/034678. Suitable FWPV include FP1, FP5, FP9, FPV M, FPV S, ATCC® VR-229, ATCC® VR-250, the USDA strain and POXVAC-TC.

In preferred embodiments of the present invention, the poxvirus is a vaccinia virus (VACV). Suitable VACV include, for example. Ankara, VACV Western Reserve (WR), VACV Copenhagen (VACV-COP), Temple of Heaven, Paris, Budapest, Dairen, Gam, MRIVP, Per, Tashkent, TBK, Tian Tan, Tom, Bem, Patwadangar, BIEM, B-15, EM-63, IHD-J, IHD-W, Ikeda, DryVax (also known as VACV Wyeth or New York City Board of Health [NYCBH] strain as for example described in U.S. Pat. No. 7,410,644), NYVAC, ACAM1000, ACAM2000, Vaccinia Lister (also known as Elstree), LC16mO, LC16m8, modified vaccinia Ankara (MVA), MVA-Vero as characterized in the International Patent Application PCT/EP01/02703 (WO 01/68820), ACAM3000 MVA, and modified vaccinia virus Ankara-Bavarian Nordic (MVA-BN).

In some embodiments, the VACV is selected from the group of DryVax, ACAM1000, ACAM2000, Lister, EM-63, VACV-COP, WR, NYCBH, NYVAC and MVA.

In some embodiments of the present invention, the poxvirus is a modified vaccinia Ankara (MVA) virus.

Modified Vaccinia Virus Ankara (MVA)

In various embodiments, the MVA or MVA used for generating the recombinants suitable for the present invention are MVA-572, MVA-575, MVA-1721, MVA as deposited as ATCC® VR-1508™, MVA as deposited as ATCC® VR-1566™, ACAM3000 MVA, MVA-BN or any similarly attenuated MVA strain. In preferred embodiments, the MVA used for generating the recombinants are MVA-575, MVA as deposited as ATCC® VR-1508™, MVA as deposited as ATCC® VR-1566™, ACAM3000 MVA and MVA-BN. More preferably the MVA used for generating the recombinants is MVA-BN.

MVA-572 was deposited at the European Collection of Animal Cell Cultures (ECACC, Vaccine Research and Production Laboratory, Public Health Laboratory Service, Centre for Applied Microbiology and Research, Porton Down, Salisbury, Wiltshire SP4 0JG, United Kingdom) with the deposition number ECACC V94012707 on Jan. 27, 1994. MVA-575 was deposited under ECACC V00120707 on Dec. 7, 2000. Acam3000 MVA was deposited at the American Type Culture Collection (ATCC) under Accession No.: PTA-5095 on Mar. 27, 2003 (American Type Culture Collection, 10801 University Blvd., Manassas, Va. 20110-2209, USA). MVA-I721 was deposited as CNCM 1721 at the Collection Nationale de Cultures de Microorganisms, Institute Pasteur. MVA-BN was deposited on Aug. 30, 2000 at the ECACC under number V00083008. MVA-BN has been described in international PCT publication WO 02/042480 (see also e.g., U.S. Pat. Nos. 6,761,893 and 6,913,752).

Also encompassed by the present invention are derivatives or variants of any of the MVA viruses or MVA-BN described herein. "Derivatives" or "variants" of MVA or MVA-BN refer to MVA or MVA-BN viruses exhibiting essentially the same replication characteristics as the MVA or MVA-BN to which it refers, but exhibiting differences in one or more parts of their genomes. Viruses having the same "replication characteristics" as the deposited virus are viruses that replicate with similar amplification ratios as the deposited strain in CEF cells and the cell lines HaCat (Boukamp et al. [1988]. J Cell Biol 106: 761-771), the human bone osteosarcoma cell line 143B (ECACC No. 91112502), the human embryo kidney cell line 293 (ECACC No. 85120602), and the human cervix adenocarcinoma cell line HeLa (ATCC No. CCL-2). Tests and assay to determine these properties of MVA, its derivatives and variants are well known to the skilled person such as the cell line permissivity assay as described in WO 02/42480. In an exemplary cell line permissivity assay mammalian cell lines are infected with the parenteral and derivative or variant MVA virus at a low multiplicity of infection per cell i.e., 0.05 infectious units per cell ($5 \times 10^4$ TCID$_{50}$). Following absorption of 1 hour the virus inoculum is removed and the cells washed three times to remove any remaining unabsorbed viruses. Fresh medium supplemented with 3% FCS are added and infections are left for a total of 4 days (at 37° C., 5% $CO_2$) where viral extracts can be prepared. The infections are stopped by freezing the plates at −80° C. for three times. Virus multiplication and cytopathic effects (CPE) are subsequently determined on CEF cells using methods well known to the skilled person such as those described in Carroll and Moss [1997], Virology 238, 198-211.

More specifically, MVA-BN or a derivative or variant of MVA-BN has preferably the capability of reproductive replication in chicken embryo fibroblasts (CEF), but no capability of reproductive replication in the human keratinocyte cell line HaCat (Boukamp et al (1988), J. Cell Biol. 106:761-771), the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, a derivative or variant of MVA-BN has a virus amplification ratio at least two fold less, more preferably three-fold less than MVA-575 in Hela cells and HaCaT cell lines. Tests and assay for these properties of MVA variants are described in WO 02/42480 or in the exemplary cell line permissivity assay as described above.

The term "not capable of reproductive replication" or "no capability of reproductive replication" is, for example, described in WO 02/42480, which also teaches how to obtain MVA having the desired properties as mentioned above. The term applies to a virus that has a virus amplification ratio at 4 days after infection of less than 1 using the assays described in WO 02/42480 or in U.S. Pat. No. 6,761,893.

The term "fails to reproductively replicate" refers to a virus that has a virus amplification ratio at 4 days after infection of less than 1. Assays described in WO 02/42480 or in U.S. Pat. No. 6,761,893 are applicable for the determination of the virus amplification ratio.

The amplification or replication of a virus is normally expressed as the ratio of virus produced from an infected cell (output) to the amount originally used to infect the cell in the first place (input) referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

In certain embodiments, the MVA comprised in any of the compositions is MVA-BN, preferably as deposited at the European Collection of Animal Cell cultures (ECACC) under accession number V00083008 or derivatives thereof.

In some embodiments, the MVA comprised in any of the compositions is a MVA-BN virus or a derivative thereof having the capability of reproductive replication in vitro in chicken embryo fibroblasts (CEF) cells, but no capability of reproductive replication in the human keratinocyte cell line HaCat, the human bone osteosarcoma cell line 143B, the human embryo kidney cell line 293, and the human cervix adenocarcinoma cell line HeLa.

In some embodiments, the MVA comprised in any of the compositions is a MVA-BN virus deposited at the European Collection of Animal Cell cultures (ECACC) under accession number V00083008 or a derivative thereof preferably having the capability of reproductive replication in vitro in chicken embryo fibroblasts (CEF) cells, but no capability of reproductive replication in the human keratinocyte cell line HaCat, the human bone osteosarcoma cell line 143B, the human embryo kidney cell line 293, and the human cervix adenocarcinoma cell line HeLa.

In preferred embodiments, the poxvirus or any preferred virus disclosed herein is a purified or partially purified virus. Methods for production and purification of a poxvirus, e.g., VACV or MVA are known to the person skilled in the art and are further described below.

The poxvirus virus of any of the embodiments can be a recombinant or non-recombinant poxvirus, preferably a recombinant vaccinia virus, more preferably a recombinant MVA. The term "recombinant" refers to a virus, more particularly a poxvirus, comprising an exogenous nucleic acid sequence inserted in its genome, which is not naturally present in the parent virus. A recombinant virus (e.g., poxvirus such as but not limited to MVA), thus refers to a nucleic acid or virus made by an artificial combination of two or more segments of nucleic acid sequence of synthetic or semisynthetic origin which does not occur in nature or is linked to another nucleic acid in an arrangement not found in nature. The artificial combination is most commonly accomplished by artificial manipulation of isolated segments of nucleic acids, using well-established genetic engineering techniques. Generally, a "recombinant" poxvirus as described herein refers to poxviruses that are produced by standard genetic engineering methods, e.g., MVAs of the present invention are thus genetically engineered or genetically modified MVAs. The term "recombinant MVA" thus includes MVAs (e.g., MVA-BN) which have stably integrated recombinant nucleic acid, preferably in the form of a transcriptional unit, in their genome. A transcriptional unit may include a promoter, enhancer, terminator and/or silencer. Recombinant MVAs of the present invention may express heterologous antigenic determinants, polypeptides or proteins (antigens) upon induction of the regulatory elements.

The term "antigenic determinant" refers to any molecule that stimulates a host's immune system to make an antigen-specific immune response, whether a cellular response or a humoral antibody response. Antigenic determinants may include proteins, polypeptides, antigenic protein fragments, antigens, and epitopes which elicit an immune response in a host and form part of an antigen, homologues or variants of proteins, polypeptides, and antigenic protein fragments, and epitopes including, for example, glycosylated proteins, polypeptides, antigenic protein fragments, antigens and epitopes, and nucleotide sequences or genes encoding such molecules. Thus, proteins, polypeptides, antigenic protein fragments, and epitopes are not limited to particular native nucleotide or amino acid sequences but encompass sequences identical to the native sequence as well as modifications to the native sequence, such as deletions, additions, insertions and substitutions.

The term "derivatives" and "variants" when used in the context of antigenic determinants preferably have at least about 50%, at least about 60% or 65%, at least about 70% or 75%, at least about 80%, 81%, 82%, 83%, 84%, 85%, 86%, 87%, 88%, or 89%, more typically, at least about 90%, 91%, 92%, 93%, or 94% and even more typically at least about 95%, 96%, 97%, 98% or 99%, most typically, at least about 99% identity with the referenced antigenic determinant in a particular protein, polypeptide, antigenic protein fragment, antigen and epitope at the level of nucleotide or amino acid sequence. Techniques for determining sequence identity between nucleic acids and amino acids are known in the art. Two or more sequences can be compared by determining their "percent identity." The percent identity of two sequences, whether nucleic acid or amino acid sequences, is the number of exact matches between two aligned sequences divided by the length of the shorter sequences and multiplied by 100.

The term "epitope" refers to a site on an antigen to which B- and/or T-cells respond, either alone or in conjunction with another protein such as, for example, a major histocompatibility complex ("MHC") protein or a T-cell receptor. Epitopes can be formed both from contiguous amino acids or noncontiguous amino acids juxtaposed by secondary and/or tertiary folding of a protein. Epitopes formed from contiguous amino acids are typically retained on exposure to denaturing solvents, while epitopes formed by tertiary folding are typically lost on treatment with denaturing solvents. An epitope typically includes at least 5, 6, 7, 8, 9, 10 or more amino acids—but generally less than 20 amino acids—in a unique spatial conformation. Methods of determining spatial conformation of epitopes include, for example, x-ray crystallography and 2-dimensional nuclear magnetic resonance. See, e.g., "Epitope Mapping Protocols" in Methods in Molecular Biology, Vol. 66, Glenn E. Morris, Ed (1996).

In certain embodiments, the recombinant virus of the present invention is a recombinant virus comprising a nucleic acid encoding an exogenous nucleic acid sequence inserted in its genome.

The term "exogenous" as it is used herein means that the referenced molecule is introduced into the virus genome. The molecule can be introduced, for example, by introduction of an encoding nucleic acid into the virus genome. Therefore, the term as it is used in reference to expressing of an exogenous nucleic acid refers to introduction of the encoding nucleic acid in an expressible form into virus. In contrast, the term "endogenous" refers to a referenced molecule that is present in the host.

In certain embodiments, the recombinant virus of the present invention is a recombinant virus comprising a nucleic acid expressing an exogenous nucleic acid sequence inserted in its genome.

As used herein, the terms "expressed", "express". "expressing". "expression" and the like which can be used interchangeable denote the transcription alone as well as both the transcription and translation of a sequence of interest. Thus, in referring to expression of a nucleotide sequence present in the form of DNA, the product resulting from this expression may be either RNA (resulting from transcription alone of the sequence to be expressed) or a polypeptide sequence (resulting from both transcription and translation of the sequence to be expressed). The term "expression" thus also includes the possibility that both RNA and polypeptide product result from said expression and remain together in the same shared milieu. For example, this is the case when the mRNA persists following its translation into polypeptide product.

According to other embodiments, the exogenous nucleic acid sequence of any of the embodiments can encode an antigen, preferably the antigen is a viral antigen or a tumor associated antigen (TAA).

Preferably, the viral antigen is derived from a virus such as for example a filovirus (preferably Marburg virus (MARV) and/or Ebola virus (EBOV) as described for example in WO 2016/034678), human Immunodeficiency virus type I (HIV-1; such as gp 120 or gp 160), Foot-and-mouth disease (FMD) virus (see WO 2016/202828), human or animal herpes viruses, preferably from HSV1 or HSV2, cytomegalovirus (CMV), Varicella Zoster Virus (VZV), or from a hepatitis virus such as hepatitis B virus (HBV) for example Hepatitis B Surface antigen or a derivative thereof (see WO 2011/015656 and WO 2013/007772), hepatitis A virus (HAV), hepatitis C virus (HCV; see WO 04/111082; preferentially non-structural HCV protein from genotype 1 b strain), hepatitis E virus (HEV), Human Papilloma Virus (HPV; see WO 90/10459, WO 95/09241, WO 98/04705, WO 99/03885, and WO 07/121894; E6 and E7 protein from the HPV16 and HPV18 strain are preferred), Respiratory Syncytial Virus (RSV; see WO 2014/019718), or Influenza virus (WO 2012/048817).

According to certain embodiments of the present invention, said antigen is preferably selected from HCV, HBV, HIV-1, HPV, RSV, EBOV and/or MARV, preferably EBOV and MARV.

In certain embodiments, the recombinant MVA and the exogenous nucleic acid sequence can be any of the recombinant MVA and nucleic acids encoding an antigenic protein or antigenic determinant of the filovirus as described in WO 2016/034678 and thus the application is fully incorporated by reference herewith. To the extent the material incorporated by reference contradicts or is inconsistent with this specification, the specification of the present invention will supersede any such material as already mentioned above. The incorporation by reference also includes the sequence listing of WO 2016/034678.

In particular embodiments, the recombinant virus of the present invention (preferably MVA) is a recombinant virus comprising a nucleic acid encoding one or more filovirus proteins (preferably one or more filovirus glycoproteins), preferably three filovirus glycoproteins.

In further particular embodiments, the filovirus glycoprotein is selected from Ebola virus Sudan (SEBOV), Ebola virus Zaire (ZEBOV), and Marburg virus (MARV).

In further particular embodiments, the filovirus glycoprotein is selected from Ebola virus Sudan (SEBOV), Ebola virus Zaire-Mayinga (ZEBOV-Mayinga), and Marburg virus Musoke (MARV-Musoke). In other particular embodiments, the recombinant virus of the present invention (preferably MVA) is a recombinant virus comprising a nucleic acid encoding the filovirus glycoproteins of SEBOV, ZEBOV-Mayinga, and MARV-Musoke.

In certain embodiments, the recombinant virus of the present invention (preferably MVA) comprises a nucleic acid further encoding a filovirus nucleoprotein, preferably a filovirus nucleoprotein of an Ebola virus, more preferably a nucleoprotein of Ebola virus Ivory Coast (NP-EBOV-CdI).

In certain preferred embodiments, the recombinant virus used in a composition according to the present invention is the recombinant MVA designated as MVA-mBN226, MVA-mB255, MVA-mBN254 as described in WO 2016/034678.

In certain embodiments, the tumor associated antigen is selected from carcinoembryonic antigen (CEA), mucin-1 (MUC-1), prostatic acid phosphatase (PAP), B7-1 (also known as CD80), intracellular adhesion molecule-1 (ICAM-1, also known as CD54), lymphocyte function-associated antigen-3 (LFA-3, also known as CD58), prostate specific antigen (PSA), HER-2, and brachyury or any combination thereof. Preferably, the TAA is selected from CEA, MUC-1. B7-1. ICAM-1, LFA-3, HER-2 and brachyury. Further details of such recombinants are for example described in WO 2015/175340 and WO 2008/045346.

Methods for Production of Non-Recombinant and Recombinant Poxviruses

Methods to obtain recombinant poxviruses (e.g., VACV or MVA) or to insert exogenous coding sequences into a poxvirus (e.g., VACV or MVA) genome are well known to the person skilled in the art. For example, methods for standard molecular biology techniques such as cloning of DNA, DNA and RNA isolation, Western blot analysis, RT-PCR and PCR amplification techniques are described in Molecular Cloning, A laboratory Manual 2$^{nd}$ Ed. (J. Sambrook et al., Cold Spring Harbor Laboratory Press (1989)), and techniques for the handling and manipulation of viruses are described in Virology Methods Manual (B. W. J. Mahy et al. (eds.), Academic Press (1996)). Similarly, techniques and know-how for the handling, manipulation and genetic engineering of poxviruses are described in Molecular Virology: A Practical Approach (A. J. Davison & R. M. Elliott (Eds.), The Practical Approach Series, IRL Press at Oxford University Press, Oxford, UK (1993), see, e.g., Chapter 9: Expression of genes by Vaccinia virus vectors); Current Protocols in Molecular Biology (John Wiley & Son. Inc. (1998), see, e.g., Chapter 16, Section IV: Expression of proteins in mammalian cells using vaccinia viral vector); and Genetic Engineering, Recent Developments in Applications, Apple Academic Press (2011), Dana M. Santos, see, e.g., Chapter 3: Recombinant-mediated Genetic Engineering of a Bacterial Artificial Chromosome Clone of Modified Vaccinia Virus Ankara (MVA)). Construction and isolation of recombinant MVA are also described in Methods and Protocols, Vaccinia Virus and Poxvirology, ISBN 978-1-58829-229-2 (Staib et al.), Humana Press (2004) see, e.g., Chapter 7.

Methods for producing and purifying virus-based material such as viral vectors and/or viruses used according to the present invention are known by the person skilled in the art. Available methods comprise the replication of the virus in CEF cells or cell lines in particular DF-1 (U.S. Pat. No. 5,879,924), EBx chicken cell line (WO 2005/007840), EB66 duck cells (WO 08/129058), or Cairina moschata immortalized avian cells (WO 2007/077256 or WO 2009/004016). They can be cultivated under conditions well known to the person skilled in the art. Serum-free methods for virus cultivation and virus amplification in CEF cells are described for example in WO 2004/022729. Upstream and downstream processes for production of virus may be obtained from WO 2012/010280 or 2016/087457. Methods as useful for purifying viruses of the present application are in detail disclosed in WO 03/054175, WO 07/147528, WO 2008/138533, WO 2009/100521 and WO 2010/130753. Exemplary methods for propagation and purification of recombinant poxvirus in duck embryo-derived cell are described in Leon et al. [2016], The EB66 cell line as a valuable cell substrate for MVA-based vaccines production, Vaccine 34:5878-5885.

In some embodiments, said composition comprises a virus titer in the range from about $1 \times 10^6$ InfU/mL to about $2 \times 10^9$ InfU/mL, preferably about $1 \times 10^7$ InfU/mL to about $2 \times 10^9$ InfU/mL, more preferably about $1 \times 10^7$ InfU/mL to about $4 \times 10^8$ InfU/mL. In certain other embodiments, the titer is in the range from about $0.1 \times 10^8$ InfU/mL to about $4 \times 10^8$ InfU/mL.

Sulfate Salt

In certain embodiments, the sulfate salt is a monovalent cation salt. A monovalent cation according to the present invention is for example a sodium cation, a potassium cation, a magnesium cation or an ammonium cation.

In certain embodiments, the sulfate salt of the present invention is selected from sodium sulfate, potassium sulfate, magnesium sulfate and/or ammonium sulfate.

In preferred embodiments, the sulfate salt is sodium sulfate, magnesium sulfate and/or ammonium sulfate, preferably sodium sulfate. In certain embodiments, the sodium sulfate salt is a monobasic and/or dibasic sulfate salt. Preferably the sulfate salt is disodium sulfate ($Na_2SO_4$) and/or sodium hydrogen sulfate ($NaHSO_4$) salt, preferably the sulfate salt is disodium sulfate ($Na_2SO_4$) salt.

In certain embodiments, the sulfate salt (e.g., sodium sulfate, potassium sulfate, magnesium sulfate and/or ammonium sulfate) concentration is between about 5 mM and 300 mM, between about 5 mM and 250 mM, between about 5 mM and 220 mM, between about 5 mM and 200 mM, between about 5 mM and 180 mM, between about 5 mM and 150 mM, between about 5 mM and 120 mM, between about 10 mM and 300 mM, between about 20 mM and 300 mM, between about 30 mM and 300 mM, between about 40 mM and 300 mM, between about 50 mM and 300 mM, between about 70 mM and 300 mM, between about 80 mM and 300 mM, between about 80 mM and 150 mM, between about 90 mM and 150 mM, between about 90 mM and 120 mM, between about 90 mM and 110 mM, between about 48 mM and 110 mM or between about 10 mM and 110 mM. In certain embodiments, the composition of the present invention comprises a sulfate salt at a concentration of about 100 mM, preferably a sodium sulfate (in particular $Na_2SO_4$ and/or $NaHSO_4$), potassium sulfate, magnesium sulfate and/or ammonium sulfate, more preferably sodium sulfate and/or ammonium sulfate, most preferably sodium sulfate.

In certain embodiments, the concentration of the sodium sulfate (in particular $Na_2SO_4$ and/or $NaHSO_4$) is in one of the concentration ranges as described above for the other sulfate salts, preferably $Na_2SO_4$ and/or $NaHSO_4$ salt in the composition as described herein is present at a concentration between about 50 and 150 mM, preferably at a concentration of about 100 mM.

In certain embodiments of the invention, the sulfate salt and any preferred sulfate salt as described herein is an inorganic salt, preferably wherein the inorganic salt does not contain a carbon atom.

In certain embodiments of the invention, the sulfate salt is a pharmaceutical acceptable sulfate salt.

In certain embodiments, the composition of the invention is free or essentially free of sodium dodecyl sulfate. The term "essentially free of sodium dodecyl sulfate" is intended to mean that sodium dodecyl sulfate, even if present, is not contributing to the stabilization of the virus in the formulation to such an extent that a person skilled in the art would judge its presence beneficial from a stabilization standpoint.

pH and Buffer

The compositions according to the present invention has a pH of between about 6.0 and 8.5, preferably of between about 6.5 and 8.5.

The certain embodiments, the compositions according to the present invention has a pH of between about 6.5 and 8.5, between about 6.6 and 8.0, between about 6.8 and 7.5, between about 6.8 and 7.2, between about 6.8 and 8.2, between about 6.9 and 8.2, between about 7.0 and 8.5, between about 7.2 and 8.2, between about 7.4 and 8.2, between about 7.6 and 8.2, or between about 7.5 and 8.5.

In order to maintain this pH, the composition according to the invention comprises a buffer with a buffering capacity at the pH of the composition. The term "buffer" or "buffer solution" as used herein, refers to an aqueous solution consisting of a mixture of a weak acid and its conjugate base, or vice versa. Its pH changes very little when a small or moderate amount of strong acid or base is added to it and thus it is used to prevent changes in the pH of a solution. Buffer solutions are used as a means of keeping pH at a nearly constant value in a wide variety of applications. For buffers in acid regions, the pH may be adjusted to a desired value by adding a strong acid such as hydrochloric acid to the buffering agent. For alkaline buffers, a strong base such as sodium hydroxide may be added. Alternatively, a buffer mixture can be made from a mixture of an acid and its conjugate base. For example, an acetate buffer can be made from a mixture of acetic acid and sodium acetate. Similarly an alkaline buffer can be made from a mixture of the base and its conjugate acid. Preferably the buffer is a pharmaceutical acceptable buffer.

Examples of buffers include but are not limited to phosphate buffer saline (e.g. PBS), phosphate buffer, citrate buffer (e.g. SSC), citrate/phosphate buffer. TES, DIPSO, TEA, EPPS, Bicine, Tris (Tris(hydroxymethyl)aminomethane), Tris-HCl (Tris(hydroxymethyl)aminomethane-HCl), Tricine (N-[tris(hydroxymethyl)methyl)-methyl]-glycine), TAPSO, HEPES, TES, MOPS, PIPES, POPSO, MES, succinic acid buffer. Phosphate-buffered saline (abbreviated PBS) is a water-based salt solution containing sodium phosphate, sodium chloride and, in some compositions, potassium chloride and potassium phosphate. Preferably the buffer is selected from the group of TRIS, TRIS-HCL, Tricine, citrate buffer, citrate/phosphate and phosphate buffer. In a further preferred embodiment, the buffer is TRIS buffer, citrate buffer, citrate/phosphate or phosphate buffer. The phosphate buffer preferably comprises a mixture of $Na_2HPO_4$ and $KH_2PO_4$ or a mixture of $Na_2HPO_4$ and $NaH_2PO_4$. The citrate/phosphate buffer preferably comprises $Na_2HPO_4$ and sodium citrate. In certain embodiments, the buffer comprises Tris buffer or phosphate buffer.

Said buffer is preferably present at a concentration of between about 5 mM and 40) mM. In certain embodiments, said buffer is present at a concentration of between about 5 mM and 25 mM, between about 8 mM and 22 mM, between about 8 mM and 15 mM mM, or between about 5 mM and 15 mM. In certain embodiments, said buffer is present at a concentration of about 10 mM.

In further preferred embodiments, said buffer is a Tris buffer at a pH ranging from about 6.5 to 8.5, preferably about 7.5 to 8.5, most preferably with a pH at about 8.0.

In further preferred embodiments, said buffer is a phosphate buffer at a pH ranging from about 6.5 to 8.5, at a pH ranging from about 6.5 to 7.5, at a pH ranging from about 7.0 to 8.5, at a pH ranging from about 6.9 to 7.6, at a pH ranging from about 7.3 to 7.6, at a pH ranging from about 6.9 to 7.2, more preferably with a pH at about 7.0, more preferably with a pH at about 7.5.

In further preferred embodiments, said buffer is a citrate buffer or citrate/phosphate buffer at a pH ranging from about 6.0 to 8.0, preferably with a pH ranging from about 6.5 to 7.5.

Other Ingredients

The composition of the present invention may further include one or more pharmaceutical acceptable and/or approved carriers, additives, antibiotics, preservatives, adjuvants, antioxidants, diluents and/or stabilizers. Such auxiliary substances can be but are not limited to one or more sugar, sugar alcohol, polyol, detergent, one or more amino acids, a viscosity enhancer, one or more additional salts, antioxidants, ethanol, EDTA, or the like.

In certain embodiments, the composition of the present invention further comprises sugar, sugar alcohol and/or polyol.

In certain other embodiments, the composition of the present invention comprises a sugar selected from the group of sucrose, lactose, mannose and trehalose.

In certain embodiments, the composition of the present invention comprises the polyol selected from sorbitol, glycerol or mannitol, preferably glycerol and/or sorbitol. In certain embodiments, the composition of the present invention comprises sorbitol. In certain embodiments, the composition of the present invention comprises glycerol.

In certain embodiments, the concentration of said sugar or sugar alcohol in any of the compositions is ranging between about 1% (w/w) to 10% (w/w). In preferred embodiments, said concentration of sugar or sugar alcohol in said composition is ranging between about 2% (w/w) to 10% (w/w), 3% (w/w) to 10% (w/w), 4% (w/w) to 10% (w/w), 1% (w/w) to 9% (w/w), 1%6 (w/w) to 8% (w/w), 1% (w/w) to 7% (w/w), 1% (w/w) to 6% (w/w), 2% (w/w) to 6% (w/w), 2.5% (w/w) to 6% (w/w), 4% (w/w) to 6% (w/w), 5% (w/w) to 7% (w/w), or is about 6% (w/w). In certain embodiments, the concentration of sucrose in said composition is about 6% (w/w).

In certain embodiments, the concentration of polyol in said composition is ranging between about 1% (w/w) to 6% (w/w). In preferred embodiments, said concentration of polyol in said composition is ranging between about 2% (w/w) to 6% (w/w), 3% (w/w) to 6% (w/w), 4% (w/w) to 6% (w/w), 1% (w/w) to 4% (w/w), 1% (w/w) to 3% (w/w), 1% (w/w) to 2.5% (w/w) or is about 5% (w/w). In certain embodiments, the concentration of glycerol in said composition is ranging between about 1% (w/w) to 6% (w/w). In preferred embodiments, said concentration of polyol in said composition is ranging between about 2% (w/w) to 6% (w/w), 3% (w/w) to 6% (w/w), 4% (w/w) to 6% (w/w), 1% (w/w) to 4% (w/w), 1% (w/w) to 3% (w/w) to 2.5% (w/w) or is about 5% (w/w). In certain embodiments, the concentration of glycerol in said composition is about ranging between about 1% (w/w) to 6% (w/w), preferably 5% (w/w).

In certain embodiments, the composition of the present invention further comprises a detergent, preferably a non-ionic detergent. Non-ionic surfactants have been shown to induce stabilization of various viruses in the liquid state (Evans et al. [2004], J. Pharm Sci. 93:2458-75, U.S. Pat. No. 7,456,009, US 2007/0161085) e.g., by reducing aggregation or are added to reduce absorption to container surfaces.

In certain embodiments, the detergent is selected from the group of polysorbate, sodium laurylsulfate and poloxamer, preferably the polysorbate is selected from the group of polysorbate-20, polysorbate-40, polysorbate-60 and polysorbate-80.

In certain embodiments, the polysorbate (in particular polysorbate-20, polysorbate-40, polysorbate-60 and polysorbate-80 has a concentration range from about 0.001% (w/w) to about 1% (w/w), preferably from about 0.001% (w/w) to about 0.5% (w/w). In preferred embodiment, the polysorbate has a concentration range from about 0.001% (w/w) to about 0.1% (w/w), from about 0.001% (w/w) to about 0.008% (w/w), from about 0.001% (w/w) to about 0.005% (w/w). The polysorbate concentration is preferably above 0.001% (w/w) but preferably less than 0.005% (w/w).

In certain embodiments, said poloxamer is selected from the group of poloxamer 182, poloxamer 188, poloxamer 121, poloxamer 331, poloxamer 338 and/or poloxamer 407.

In certain embodiments, the poloxamer concentration (in particular poloxamer 182, poloxamer 188, poloxamer 121, poloxamer 331, poloxamer 338 and/or poloxamer 407) is ranging between about 0.001% (w/w) and 1% (w/w), preferably between about 0.005% (w/w) and 0.5% (w/w), between about 0.01% (w/w) and 0.1% (w/w), between about 0.01% (w/w) and 0.05% (w/w), between about 0.015% (w/w) and 0.03% (w/w), or is about 0.025% (w/w).

In certain embodiments, the composition of the present invention further comprises an amino acid, preferably wherein the amino acid is selected from the group of arginine, glycine, alanine, lysine, proline, histidine, glutamate, glutamic acid and aspartic acid or any combination thereof. In preferred embodiments, the amino acid is selected from glutamic acid, arginine, or glycine. The amino acid is preferably an L-isomer, preferably an L-arginine, L-glycine and or L-histidine. Said amino acid(s) is/are not an amino acid encoded by the recombinant or non-recombinant virus of the present invention. Thus, the amino acid is not contained in the composition through the process of purification of the virus (e.g., VACV or MVA) but added during the generation of the composition for manufacturing a vaccine.

The amino acid is preferably present in the composition at a concentration of between about 0.1% (w/w) and about 10% (w/w), preferably between about 0.1% (w/w) and about 5% (w/w). In further embodiment, the amino acids is preferably present in the composition at a concentration of between about 0.1% (w/w) and about 2.5% (w/w), preferably between about 2.0% (w/w) and about 5% (w/w).

Amino acids, and in particular histidine, arginine or methionine, have been found to induce stabilization of various viruses in the liquid state (see EVANS et al. J Pharm Sci. 2004 October, 93(10):2458-75, U.S. Pat. No. 7,456,009, US 2007/0161085, U.S. Pat. No. 7,914,979, WO 2014/029702, WO 2014/053571). When histidine is present in a liquid composition in order to improve stability, histidine is generally present at a concentration of at least 5 mM, and preferably at least 10 mM (see EVANS et al. J Pharm Sci. 2004 October, 93(10):2458-75, U.S. Pat. No. 7,456,009, WO 2014/029702). When arginine is present in a liquid composition in order to improve stability, arginine is generally present at a concentration of at least 50 mM (see US 2007/0161085, at least 1% (w/v) arginine corresponding to at least about 57.4 mM), and sometimes preferably at least 150 mM, and in particular about 300 mM (see WO 2014/029702). When methionine is present in a liquid composition in order to improve stability, methionine is generally present at a concentration of at least 25 mM, and preferably about 67 mM (see WO 2014/029702).

In certain embodiments, the amino acid (preferably arginine, more preferably L-arginine) is present at a concentration lower than 300 mM, preferably lower than 150 mM, lower than 100 mM, lower than 75 mM, or even lower than 50 mM. Also, when methionine is present in liquid compositions according to the invention, it is preferably present at a concentration lower than 60 mM, preferably lower than 50 mM, lower than 40 mM, lower than 30 mM, or even lower than 25 mM. More generally, when one or more amino acids is/are present in the composition according to the invention, the amino acid or amino acids is/are preferably present at a concentration lower than 300 mM, preferably lower than 150 mM, lower than 100 mM, lower than 75 mM, lower than 50 mM, lower than 40 mM, lower than 30 mM, lower than 25 mM, lower than 20 mM, lower than 10 mM, lower than 9 mM, lower than 8 mM, lower than 7.5 mM, lower than 7 mM, lower than 6 mM, or even lower than 5 mM.

In certain embodiments, the composition of the present invention is free of histidine, arginine and/or glutamic acid.

In certain embodiments, the composition of the present invention further comprises one or more additional pharmaceutical additives such as viscosity enhancer. A viscosity enhancer according to the present invention includes but is not limited to polyethyleneglycol (PEG), cellulose such as methylcellulose (MC) or carboxymethylcellulose (CMC), gelatin, agar, and/or agarose and its derivatives. For example, the concentration of the viscosity enhancer can range between about 0.1% (w/w) and 10% (w/w), preferably between about 1% (w/w) and 5% (w/w) of the composition of the present invention.

Furthermore, a viscosity enhancer can increase the viscosity of the solution.

In certain embodiments of the present invention the composition further comprises an adjuvant.

In certain embodiments, the composition of the present invention further comprises a pharmaceutical acceptable salt. In certain preferred embodiments, the salt is sodium chloride (NaCl). Sodium chloride is preferably present in the composition of the present invention at a concentration of between about 10 mM and 100 mM, preferably between about 20 mM and 100 mM, between about 40 mM and 100 mM, or between about 50 mM and 100 mM. In a preferred embodiment, sodium chloride is present at a concentration of about 70 mM.

In certain embodiments, the composition of the present invention further comprises one or more antioxidants.

In certain embodiments, the antioxidant is selected from the group of methionine, ascorbic acid, alpha tocopherol, ascorbic acid, ascorbyl palmitate, ascorbyl stearate, anoxomer; butylated hydroxyanisole, butylated hydroxytoluene, citric acid, citrates, and tertiary butyl hydroquinone. An antioxidant excipient may be present at a concentration of 0.01% (w/w), 0.05% (w/w), 0.1% (w/w), 0.5% (w/w), 1% (w/w), 2% (w/w), 3% (w/w), 4% (w/w), 5% (w/w), 6% (w/w), 7% (w/w), 8% (w/w), 9% (w/w), 10% (w/w) of the poxvirus composition, including all values and ranges in between.

In certain embodiments, the composition of the present invention further comprises a chelating agent, preferably a pharmaceutical acceptable chelating agent. The chelating agent can further improve stability of the composition in particular in liquid state.

In certain embodiments, the chelating agent is selected from ethylenediaminetetraacetic acid (EDTA), 1,2-bis(o-aminophenoxy)ethane-N,N,N',N'-tetraacetic acid (BAPTA), ethylene glycol tetraacetic acid (EGTA), dimercaptosuccinic acid (DMSA), diethylene triamine pentaacetic acid (DTPA), and 2,3-Dimercapto-1-propanesulfonic acid (DMPS), preferably said chelating agent is EDTA.

In certain embodiments, the chelating agent is present at a concentration of at least 50 µM, preferably at a concentration ranging from 50 µM to 1 mM, 50 µM to 750 µM, 50 µM to 500 µM, 50 µM to 250 µM, 50 µM to 150 µM, 50 µM to 100 µM, 50 µM to 75 µM, 100 µM to 300 µM, 100 µM to 250 µM, 100 µM to 200 µM, 100 µM to 150 µM, 150 µM to 1 mM, 150 µM to 750 µM, 150 µM to 500 µM, or 150 µM to 250 µM, preferably said chelating agent may be present at a concentration ranging from 50 µM to 150 µM.

In certain embodiments, the composition of the present invention further comprises ethanol. In certain embodiments, the composition of the present invention further comprises ethanol at a concentration ranging from 0.05% (v/v) to 5% (v/v), preferably at a concentration ranging from 0.01% (v/v) to 5% (v/v), 0.01% (v/v) to 2.5% (v/v), 0.01% (v/v) to 1.5% (v/v), 0.1% (v/v) to 5% (v/v), 0.1% (v/v) to 2.5% (v/v), 0.1% (v/v) to 1.5% (v/v), or 0.25% (v/v) to 0.75% (v/v).

Osmolality

In some embodiments, the composition of the invention has an ionic strength which is physiologically acceptable to the host. A purpose of inclusion of a salt in the composition is to attain the desired ionic strength or osmolality to stabilize the composition as well as reducing side effects or local reactions at the site of injection of the composition as a vaccine. In some embodiments, the composition of the invention has a total osmolality (the total number of molecules in solution) ranging from about 200 mOsm/L to about 1000 mOsm/L, ranging from about 200 mOsm/L to about 900 mOsm/L, from about 200 mOsm/L to about 800 mOsm/L, from about 200 mOsm/L to about 700 mOsm/L, from about 200 mOsm/L to about 600 mOsm/L, from about or 200 mOsm/L to about 500 mOsm/L. In some embodiments, the composition of the invention has a total osmolality ranging from about 250 mOsm/L to about 450 mOsm/L, preferably of about 300 mOsm/L. The osmolality as described both promotes long term storage at temperatures of 2° C.-8° C., or higher, while also making the composition suitable for parenteral, especially intramuscular or subcutaneous injection. Contributions to ionic strength may come from ions produced by the buffering compound as well as from the ions of non-buffering salts. Preferably the osmolality and ion concentrations of the solutions match those of the human body (isotonic).

Further Preferred Compositions

In one embodiment, the invention provides a composition comprising a) a poxvirus; b) a buffer; and c) a sulfate salt at a concentration of between about 5 mM and about 300 mM, wherein the composition has a pH of about 6.0 to about 8.5, preferably, the poxvirus is MVA, more preferably the poxvirus is a MVA expressing a filovirus antigen.

In another embodiment according to the invention, the composition comprises a Tris buffer or a phosphate buffer at a concentration between about 5 mM and 25 mM, a sodium sulfate concentration of between about 5 and 150 mM, wherein said composition has a pH of ranging between about 7.0 and 8.5.

In another embodiment according to the invention, the composition comprises Tris buffer at a concentration between about 5 mM and 25 mM, a sodium sulfate concentration of between about 5 and 150 mM, wherein said composition has a pH of ranging between about 7.5 and 8.5.

In another embodiment according to the invention, the composition comprises a Tris buffer at a concentration of between about 8 mM and 12 mM, and a sodium sulfate concentration of between 80 mM and 100 mM, wherein said composition has a pH ranging between about 7.7 and 8.2.

In another embodiment according to the invention, the composition comprises a Tris buffer at a concentration between about 8 mM and 12 mM, sodium sulfate at a concentration ranging between 90 mM and 110 mM with or without 4% (w/w) to 6% (w/w) sucrose or glycerol, wherein said composition has a pH ranging between about 7.6 and 8.2.

In another embodiment according to the invention, the composition comprises a Tris buffer at a concentration between about 8 mM and 12 mM, sodium sulfate at a concentration between about 45 mM and 55 mM and sodium chloride at a concentration between about 60 mM and 80 mM, wherein said composition has a pH ranging between about 7.6 and 8.0.

In another embodiment according to the invention, the composition comprises a Tris buffer at a concentration of about 10 mM, a sodium sulfate concentration of about 100 mM, wherein said composition has a pH of about 8.

In another embodiment according to the invention, the composition comprises a Tris buffer at a concentration of about 10 mM, sodium sulfate at a concentration of about 100 mM with 4% (w/w) to 6% (w/w) sucrose or glycerol, wherein said composition has a pH of about 8.

In another embodiment according to the invention, the composition comprises a Tris buffer at a concentration of about 10 mM, sodium sulfate at a concentration of about 100 mM, and sucrose at a concentration of about 6% (w/w), wherein said composition has a pH of about 8.

In another embodiment according to the invention, the composition comprises a Tris buffer at a concentration of about 10 mM, sodium sulfate at a concentration of about 100 mM, and glycerol at a concentration of about 5% (w/w), wherein said composition has a pH of about 8.

In another embodiment according to the invention, the composition comprises a Tris buffer at a concentration of about 10 mM, sodium sulfate at a concentration of about 50 mM and about 70 mM sodium chloride, wherein said composition has a pH of about 7.7.

In another embodiment according to the invention, the composition comprises a phosphate buffer at a concentration between about 5 mM and 25 mM, a sodium sulfate concentration of between about 5 and 150 mM, wherein said composition has a pH ranging between about 6.8 and 7.5.

In another embodiment according to the invention, the composition comprises a phosphate buffer at a concentration between about 7.5 mM and 12 mM, sodium sulfate at a concentration between about 90 mM and 110 mM, wherein said composition has a pH ranging between about 6.8 and 7.2.

In another embodiment according to the invention, the composition comprises a phosphate buffer at a concentration of about 10 mM, sodium sulfate at a concentration of about 100 mM, wherein said composition has a pH ranging between about 6.8 and 7.8.

In another embodiment according to the invention, the composition comprises a phosphate buffer at a concentration of about 10 mM, sodium sulfate at a concentration of about 100 mM, wherein said composition has a pH of about 7.

In another embodiment according to the invention, the composition comprises a phosphate buffer at a concentration of about 10 mM, sodium sulfate at a concentration of about 100 mM, wherein said composition has a pH of about 7.5.

In another embodiment according to the invention, the composition comprises a phosphate buffer at a concentration between about 7.5 mM and 12 mM, sodium sulfate at a concentration between about 90 mM and 110 mM, with or without 4% (w/w) to 6% (w/w) sucrose or glycerol, wherein said composition has a pH ranging between about 6.8 and 7.2.

In another embodiment according to the invention, the composition comprises a phosphate buffer at a concentration of about 10 mM, sodium sulfate at a concentration of about 100 mM, with or without 4% (w/w) to 6% (w/w) sucrose or glycerol, wherein said composition has a pH of about 7.

In another embodiment according to the invention, the composition comprises a phosphate buffer at a concentration of about 10 mM, sodium sulfate at a concentration of about 100 mM, and sucrose at a concentration of about 6% (w/w), wherein said composition has a pH of about 7.

In another embodiment according to the invention, the composition comprises a phosphate buffer at a concentration of about 10 mM, sodium sulfate at a concentration of about 100 mM, and glycerol at a concentration of about 5% (w/w), wherein said composition has a pH of about 7.

In another embodiment according to the invention, the composition comprises a phosphate buffer at a concentration of about 10 mM, sodium sulfate at a concentration of about 100 mM with or without 4% (w/w) to 6% (w/w) sucrose or glycerol, wherein said composition has a pH of about 7.5.

In another embodiment according to the invention, the composition comprises a phosphate buffer at a concentration of about 10 mM, sodium sulfate at a concentration of about 100 mM, and glycerol at a concentration of about 5% (w/w), wherein said composition has a pH of about 7.5.

In certain embodiments, the invention relates to a pharmaceutical composition comprising the composition of any of the embodiments as described herein.

In certain embodiments, the pharmaceutical composition comprising the composition of any of the embodiments is a pharmaceutical composition suitable for parenteral administration.

In certain embodiments of the invention, the pharmaceutical composition comprising the composition of any of the embodiments is a pharmaceutical composition suitable for intramuscular, subcutaneous, intravenous, or intranasal application.

In certain embodiments the composition according to the present invention is contained in a vial. The term "vial" refers to any container, vessel, cartridge, device, glass ampoule, or syringe capable for storage of active pharmaceutical ingredients such as the viruses as disclosed herein. The terms vial, container, vessel, cartridge, device, glass ampoule, or syringe can thus be used interchangeably. The vial is usually made of inert material, in particular glass (such as DIN 2R type I borosilicate glass viral) or polymeric material. In a preferred embodiment the composition is contained in a syringe.

The composition of the present invention can be administered to the subject preferably a human by any means known in the art. The routes of administration include but are not limited to intramuscular injection, subcutaneous injection, intradermal injection, intravenous application, intranasal administration, transdermal administration, transcutaneous administration, or percutaneous administration. The mode of administration, the dose and the number of administrations can be optimized by those skilled in the art in a known manner.

In certain embodiments, the composition of the present application comprises the virus in a dose range of $10^4$ to $10^9$ $TCID_{50}$/mL, $10^5$ to $5\times10^8$ $TCID_{50}$/mL, $10^6$ to $10^8$ $TCID_{50}$/mL, or $10^7$ to $10^8$ $TCID_{50}$/mL. A preferred dose for the subjects (preferably a human) comprises between $10^6$ to $10^9$ $TCID_{50}$, including a dose of $10^6$ $TCID_{50}$, $10^7$ $TCID_{50}$, or $10^8$ $TCID_{50}$. Preferably, the dose for humans comprises at least $2\times10^7$ $TCID_{50}$, at least $3\times10^7$ $TCID_{50}$, at least $5\times10^7$ $TCID_{50}$, at least $1\times10^8$ $TCID_{50}$, at least $2\times10^8$ $TCID_{50}$, preferably in a volume of 0.1 mL to 0.5 mL.

The present invention also relates to a composition or pharmaceutical composition of any of the embodiments of the present invention for treating and/or preventing of diseases or against a pathogen, preferably a disease is chosen from cancer or infectious disease.

The present invention also relates to the use of a composition or pharmaceutical composition of any of the embodiments of the present invention for manufacturing a medicament for treating and/or preventing of diseases or against a pathogen, preferably a disease chosen from cancer or infectious disease.

Another embodiment concerns a method for the vaccination of a subject (preferably a human) in need thereof, with the composition or pharmaceutical composition of any of the embodiments of the present invention.

Another embodiment relates to a method for treating and/or preventing a disease or against a pathogen preferably a disease chosen from cancer or infectious disease comprising administering the composition or pharmaceutical composition as described herein to a subject (preferably a human) in need thereof.

In certain embodiments the invention relates to a method of stabilizing a poxvirus composition comprising preparing a composition of any of the embodiments.

In certain embodiments the invention relates to a method of stabilizing a poxvirus composition comprising a step of preparing a composition of any of the embodiments and storing said composition at a temperature ranging between 2 degrees centigrade and 8 degrees centigrade.

In certain embodiments the invention relates to a method of stabilizing a poxvirus composition comprising a step of adding a sulfate salt at a concentration between about 5 mM and 300 mM to a poxvirus composition, preferably adding a sulfate salt at a concentration between about 10 mM and 140 mM.

In certain embodiments the invention relates to a method of stabilizing a poxvirus composition of any of the embodiments, wherein the poxvirus composition comprises a buffer and wherein said composition has a pH of between about 6.5 and 8.5.

The detailed examples which follow are intended to contribute to a better understanding of the present invention. However, the invention is not limited by the examples. Other embodiments of the invention will be apparent to those skilled in the art from consideration of the specification and practice of the invention disclosed herein.

EXAMPLES

Example 1

Preparation of Liquid Poxvirus Containing Drug Substance

The MVA-BN-FILO (MVA-mBN266) as used in the following examples has been in detail described in WO 2016/034678. The MVA encodes for three filovirus glycoproteins, the glycoprotein of Ebola virus Sudan (GP-SEBOV), of Ebola virus Zaire-Mayinga (GP-ZEBOV-Mayinga), and of Marburg virus Musoke (GP-MARV-Musoke) and the nucleoprotein of Ebola virus Ivory Coast (NP-EBOV-CdI). Expression cassettes for GP-ZEBOV-Mayinga and GP-MARV-Musoke were inserted into the intergenic region IGR 148/149. The expression cassette for GP-SEBOV and NP-EBOV-CdI was inserted into the intergenic region IGR 88/89 under poxvirus promoters as described in WO 2016/034678. The recombinant virus was purified using standard methods known to the skilled person. The MVA-BN-FILO bulk drug substance (BDS) with a virus concentration of $5\times10^8$ InfU/mL was stored in 10 mM Tris, with 140 mM NaCl at pH 7.7. In order to improve stability of the product at 2° C. to 8° C., more than 200 different formulations have been analysed using a variety of salts, sugar additives, amino acids and buffers. The best results were obtained with sodium sulfate ($Na_2SO_4$).

Example 2

Effect of pH, Buffer and Sulfate

MVA-BN-FILO BDS has been buffer-exchanged using ultrafiltration/dia-filtration into MilliQ grade water. Thereafter, specific volumes of concentrated Tris buffer (at different pH) and sodium sulfate ($Na_2SO_4$) solutions were spiked in order to obtain the end formulation. This formulation, Formulation B, consisted of 10 mM Tris buffer and 100 mM $Na_2SO_4$ and was divided into Formulations B1, B2, B3, and B4 with pH 7.5, 8, 8.5 and 9 respectively.

The same compositions without the 100 mM $Na_2SO_4$ (Formulations A1, A2, A3 and A4) were taken along as comparators. Table 1 gives an overview of the prepared formulations. All the formulations had a MVA virus potency titer of $3.75\times10^8$ InfU/mL.

TABLE 1

Composition of the formulations prepared in this study.

| | Composition |
|---|---|
| Formulation A1 | 10 mM Tris pH 7.5 |
| Formulation A2 | 10 mM Tris pH 8 |
| Formulation A3 | 10 mM Tris pH 8.5 |
| Formulation A4 | 10 mM Tris pH 9 |
| Formulation B1 | 10 mM Tris pH 7.5 + 100 mM $Na_2SO_4$ |
| Formulation B2 | 10 mM Tris pH 8 + 100 mM $Na_2SO_4$ |
| Formulation B3 | 10 mM Tris pH 8.5 + 100 mM $Na_2SO_4$ |
| Formulation B4 | 10 mM Tris pH 9 + 100 mM $Na_2SO_4$ |

Each formulation was subjected to an accelerated stress condition for 1 week at 25° C., a condition which was known to lead to degradation of the MVA. The samples were measured before and after applying accelerated stress. Measurements of the anisotropy (FIG. 1) and the intrinsic fluorescence (noted in FIG. 2 as emission peak shift and emission intensity change), were performed on a Fluoromax 4 spectrofluorometer (Jobin Yvon Horiba, UK). Dynamic light scattering measurements (noted in FIG. 2 as Z-average diameter change and polydispersity index (PDI) change) were performed on a Zetasizer. In addition, also the pH was measured before and after applying accelerated stress.

Results and Conclusion

The results of the anisotropy measurements are shown in FIG. 1. It was shown that all the anisotropy scans changed after applying accelerated stress. For all the formulations the anisotropy scans decreased after stress, which indicates that the excited groups in the proteins of the MVA became more flexible. This increase in flexibility can be assigned to unfolding of those particular groups of the protein and/or dissociation of the protein constructs. However, the extent of this change was less pronounced when there was sulfate present in the solution. In addition, changes were similar at different pH in sulfate-containing formulation, indicating a robust stabilizing effect of sulfate. Given the fact that the anisotropy is independent of the protein concentration and light scattering, this indicates that the results obtained with this method are highly reliable.

Figure 2:
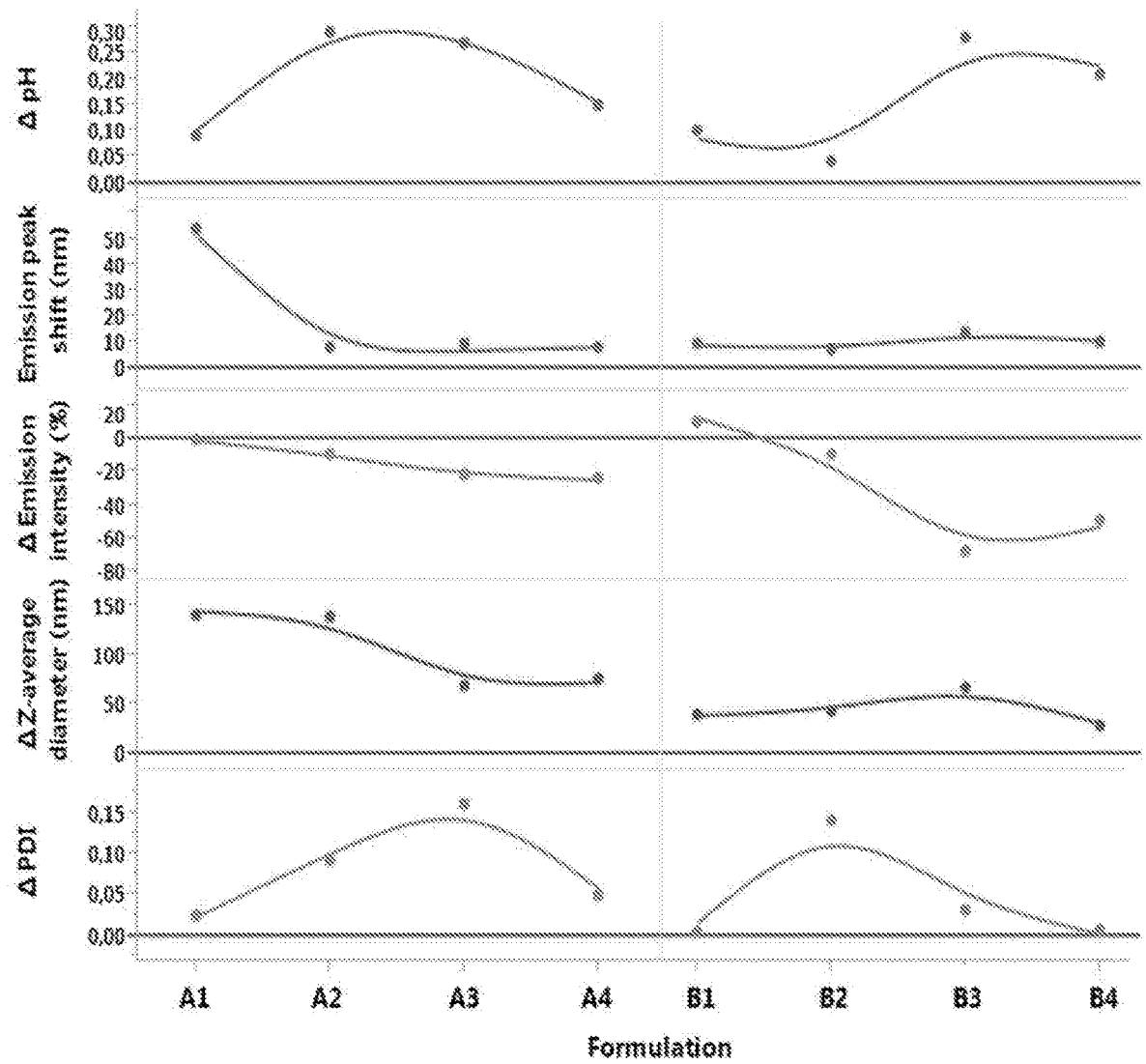

FIG. 2 shows the results of pH change, emission peak shift, emission intensity change, change in the Z-average diameter and the polydispersity index (PDI) after accelerated stress of Formulations A1-A4 (without $Na_2SO_4$) and B1-B4 (with $Na_2SO_4$). The presence of sulfate has a pronounced effect on the colloidal stability which can be seen from the changes in Z-average diameter and PDI, which were lower in the sulfate containing formulations. The improved colloidal stability denotes that the particulate mixture does not easily aggregate or dissociate. Because of the correlation between colloidal instability for MVA-BN-FILO and a decreased potency of the virus the improved colloidal stability positively influences the activity of the virus. The observed change in pH and emission intensity was limited, in particular at pH 7.5 and 8.0 for the formulations containing $Na_2SO_4$. As the emission intensity can be affected by the scattering properties of the sample, the emission intensity can decrease due to the fact that the scattering property of the sample increased. In contrast to the emission intensity, the peak shift does not depend on the scattering of light and the results show that the peak shift is low for all sulfate formulations. This indicates that the conformational changes in the protein structure are limited in these formulations and that the sulfate has a robust stabilizing effect.

Example 3

Experimental Design and Methodology

In order to further investigate the effect of sulfate on the stability of the MVA virus, we have tested several additional formulations with different salts. An overview of these additional formulations is shown in Table 2.

TABLE 2

Composition of the tested formulations

| | Composition |
|---|---|
| Formulation A1 | 10 mM Tris pH 7.5 |
| Formulation A2 | 10 mM Tris pH 8 |
| Formulation A3 | 10 mM Tris pH 8.5 |
| Formulation A4 | 10 mM Tris pH 9 |
| Formulation B1 | 10 mM Tris pH 7.5 + 100 mM $Na_2SO_4$ |
| Formulation B2 | 10 mM Tris pH 8 + 100 mM $Na_2SO_4$ |
| Formulation B3 | 10 mM Tris pH 8.5 + 100 mM $Na_2SO_4$ |
| Formulation B4 | 10 mM Tris pH 9 + 100 mM $Na_2SO_4$ |
| Formulation C1 | 10 mM Tris pH 7.5 + 100 mM $CaCl_2$ |
| Formulation C2 | 10 mM Tris pH 8 + 100 mM $CaCl_2$ |
| Formulation C3 | 10 mM Tris pH 8.5 + 100 mM $CaCl_2$ |
| Formulation C4 | 10 mM Tris pH 9 + 100 mM $CaCl_2$ |
| Formulation D1 | 10 mM Tris pH 7.5 + 100 mM $MgSO_4$ |
| Formulation D2 | 10 mM Tris pH 8 + 100 mM $MgSO_4$ |
| Formulation D3 | 10 mM Tris pH 8.5 + 100 mM $MgSO_4$ |
| Formulation D4 | 10 mM Tris pH 9 + 100 mM $MgSO_4$ |
| Formulation E1 | 10 mM Tris pH 7.5 + 100 mM $MgCl_2$ |
| Formulation E2 | 10 mM Tris pH 8 + 100 mM $MgCl_2$ |
| Formulation E3 | 10 mM Tris pH 8.5 + 100 mM $MgCl_2$ |
| Formulation E4 | 10 mM Tris pH 9 + 100 mM $MgCl_2$ |
| Formulation F1 | 10 mM Tris pH 7.5 + 140 mM NaCl |
| Formulation F2 | 10 mM Tris pH 8 + 140 mM NaCl |
| Formulation F3 | 10 mM Tris pH 8.5 + 140 mM NaCl |
| Formulation F4 | 10 mM Tris pH 9 + 140 mM NaCl |

Each formulation was subjected to an accelerated stress condition (1 day at 37° C.) that was known to lead to degradation of the MVA. Samples were taken from each formulation and were measured before and after applying accelerated stress. Measurements of the turbidity were performed on a BioTek Neo plate reader. Dynamic light scattering (DLS) (noted as Z-average diameter change and PDI change) measurements were performed on the Zetasizer.

Results and Conclusion

Figure 3:
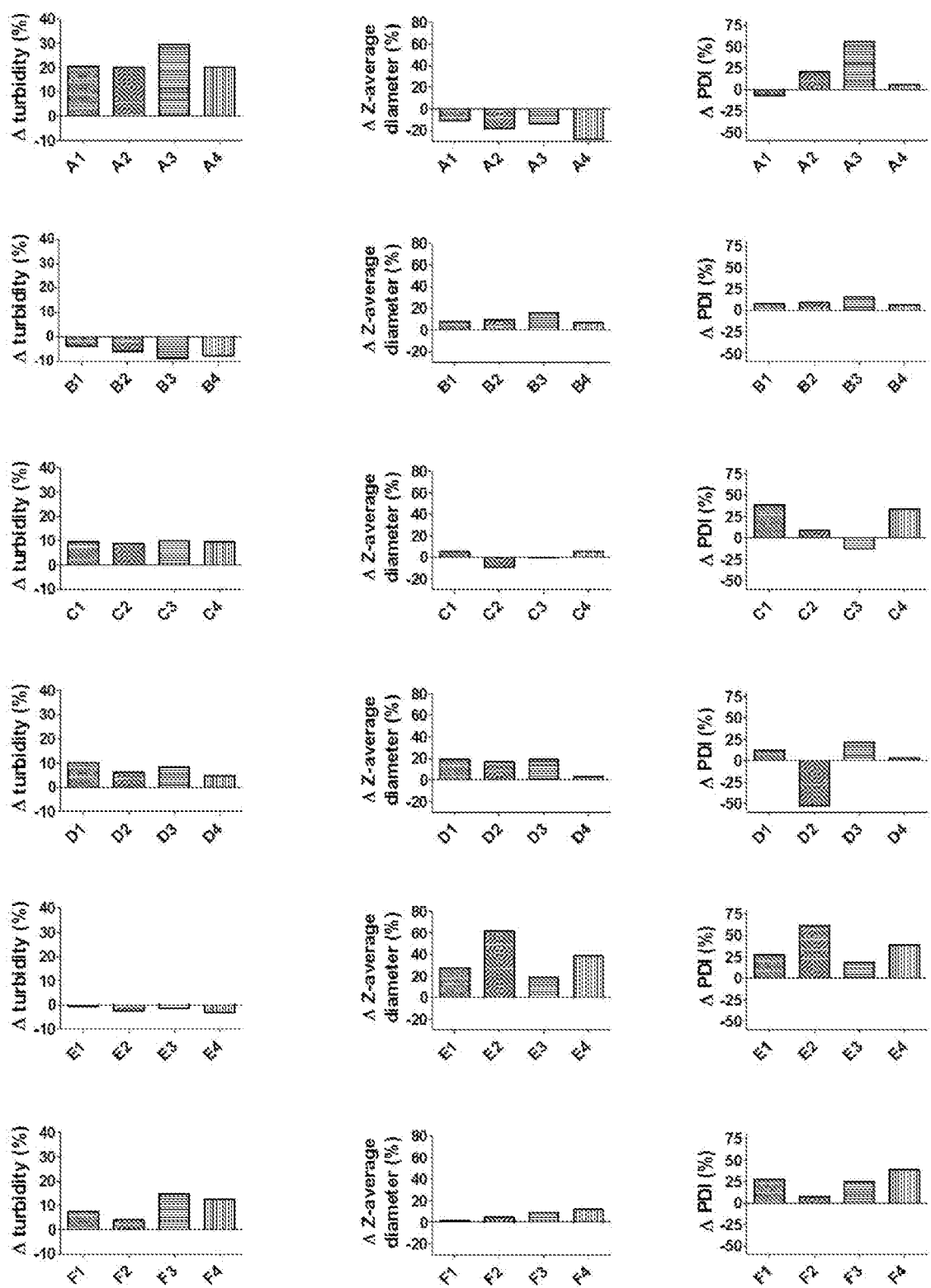

An overview of all the results obtained in this experiment is shown in FIG. 3. Each graph represents the results obtained per formulation at different pH. Each column of graphs shows measurements obtained with a separate assay.

It is seen from the turbidity results that $MgCl_2$ containing formulations (formulations E1-4) show the least changes after accelerated stress followed by $Na_2SO_4$ formulations (formulations B1-4) and $MgSO_4$ formulations (formulations D1-4), who seem to have undergone limited changes in turbidity. It should be noted that the turbidity is a result of overall scattering of light due to the presence of particles in solution. The extent of this scattering, or turbidity, depends on many factors, among others particle size, particle concentration, and particle shape. Additional information on the colloidal is provided by DLS results (Z-average diameter and PDI).

The changes in Z-average diameter after accelerated stress are the lowest for $CaCl_2$ containing formulations (formulations C1-4). However, the initial Z-average diameters in these formulations were over 900 nm. This is relatively high for a MVA formulation (MVA having a size of about 200 nm), indicating the presence of initial aggregation before accelerated stress was applied. Disregarding the results of CaCl$_2$ containing formulations, NaCl containing formulations (formulations F1-4) showed the least changes in Z-average diameter after stress. Interestingly, the Na$_2$SO$_4$ formulations (formulations B1-4) seem to perform as well as the NaCl containing formulations, followed by MgSO$_4$ formulations (formulations D1-4). This observation shows that the presence of sulfate in the formulation improves the colloidal stability. In contrast to MgSO$_4$, the presence of MgCl$_2$ (E1-4) seems to have a negative effect on the Z-average diameter, independent of the pH tested. Looking to the changes in the PDI the Na$_2$SO$_4$ formulations (formulations B1-4) showed the least changes, followed by MgSO$_4$ formulations (formulations D1-4) and NaCl containing formulations (formulations F1-4). The same explanation as given above for the changes in Z-average diameter can also be applied for the PDI results, indicating that the presence of sulfate is crucial and Na$_2$SO$_4$ is most preferred based on the data shown.

Example 4

Experimental Design and Methodology

In this study the effect of the same salts as in Example 3 were tested in a phosphate buffer at different pH. An overview of these additional formulations is shown in Table 3.

Each formulation was subjected to an accelerated stress condition (1 day at 37° C.). The samples were measured before and after applying accelerated stress. Measurements of the turbidity were performed on a BioTek Neo plate reader. Dynamic light scattering (DLS) (noted as Z-average diameter change and PDI change) measurements were performed on the Zetasizer.

TABLE 3

Composition of the tested formulations

| | Composition |
|---|---|
| Formulation A1 | 10 mM phosphate pH 7 |
| Formulation A2 | 10 mM phosphate pH 7.5 |
| Formulation A3 | 10 mM phosphate pH 8 |
| Formulation A4 | 10 mM phosphate pH 8.5 |
| Formulation B1 | 10 mM phosphate pH 7 + 100 mM Na$_2$SO$_4$ |
| Formulation B2 | 10 mM phosphate pH 7.5 + 100 mM Na$_2$SO$_4$ |
| Formulation B3 | 10 mM phosphate pH 8 + 100 mM Na$_2$SO$_4$ |
| Formulation B4 | 10 mM phosphate pH 8.5 + 100 mM Na$_2$SO$_4$ |
| Formulation C1 | 10 mM phosphate pH 7 + 100 mM MgCl$_2$ |
| Formulation C2 | 10 mM phosphate pH 7.5 + 100 mM MgCl$_2$ |
| Formulation C3 | 10 mM phosphate pH 8 + 100 mM MgCl$_2$ |
| Formulation C4 | 10 mM phosphate pH 8.5 + 100 mM MgCl$_2$ |
| Formulation D1 | 10 mM phosphate pH 7 + 140 mM NaCl |
| Formulation D2 | 10 mM phosphate pH 7.5 + 140 mM NaCl |
| Formulation D3 | 10 mM phosphate pH 8 + 140 mM NaCl |
| Formulation D4 | 10 mM phosphate pH 8.5 + 140 mM NaCl |

Results and Conclusion

Figure 4:
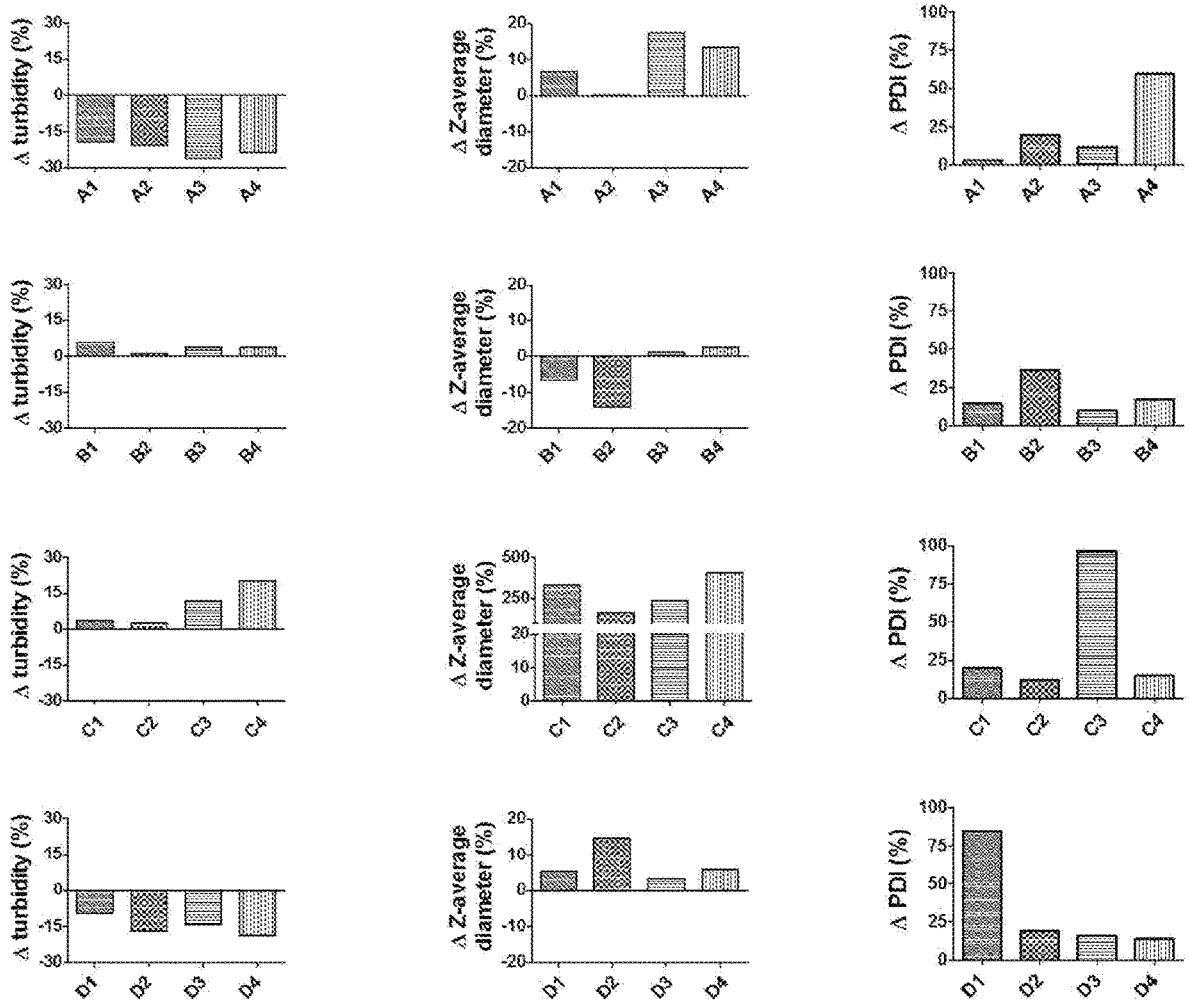
Figure 5:
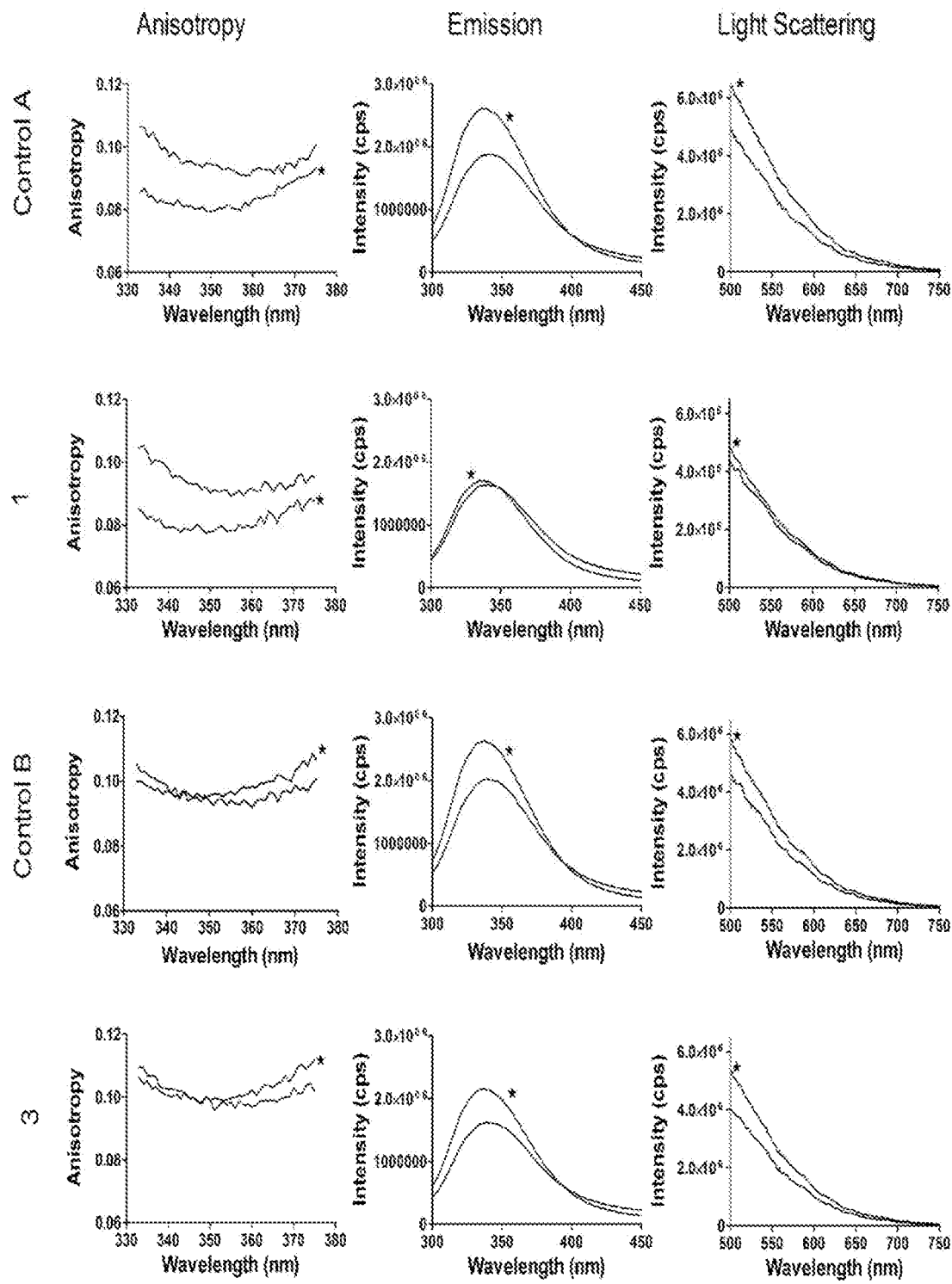
Figure 6:
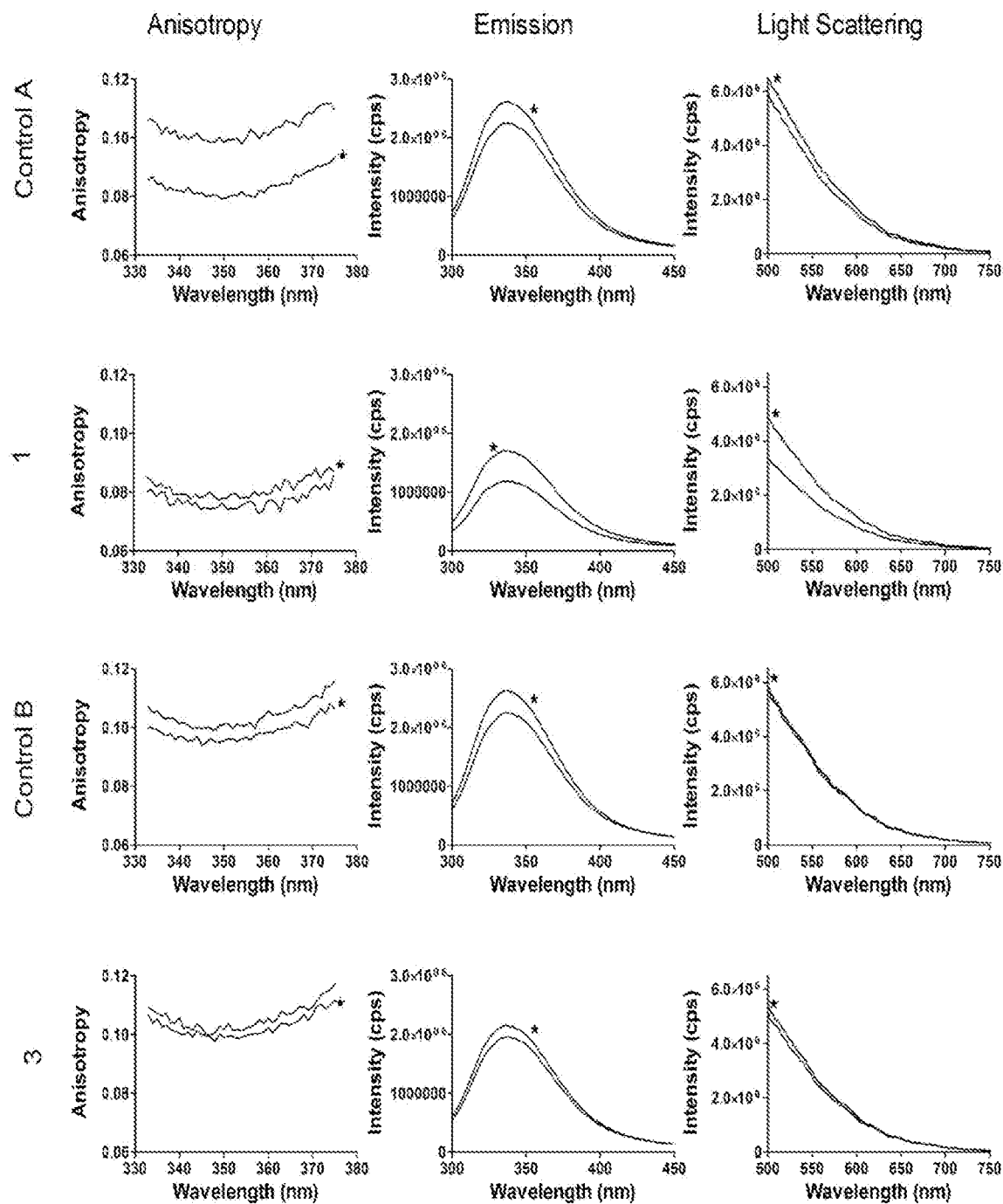
Figure 7:
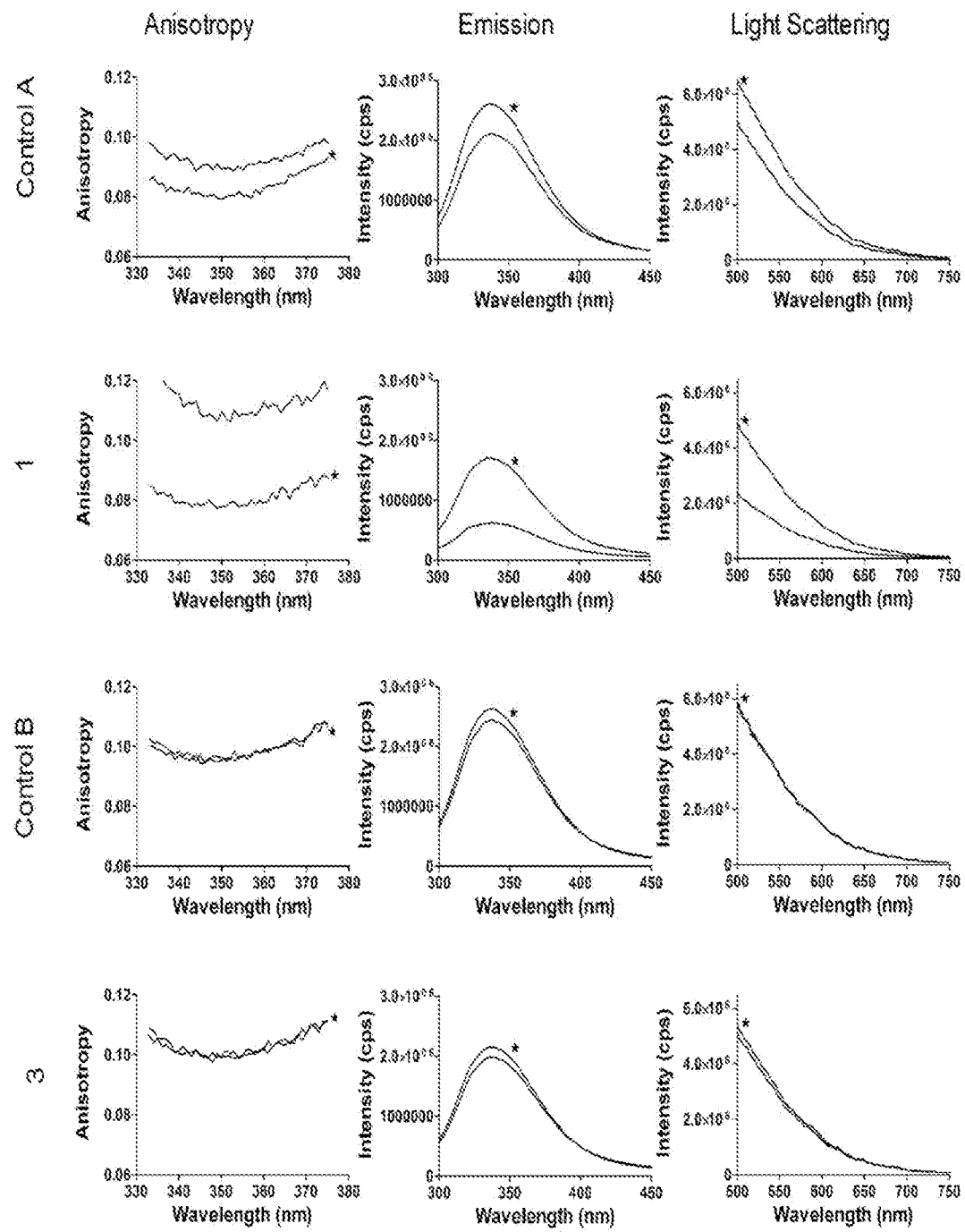
Figure 8:
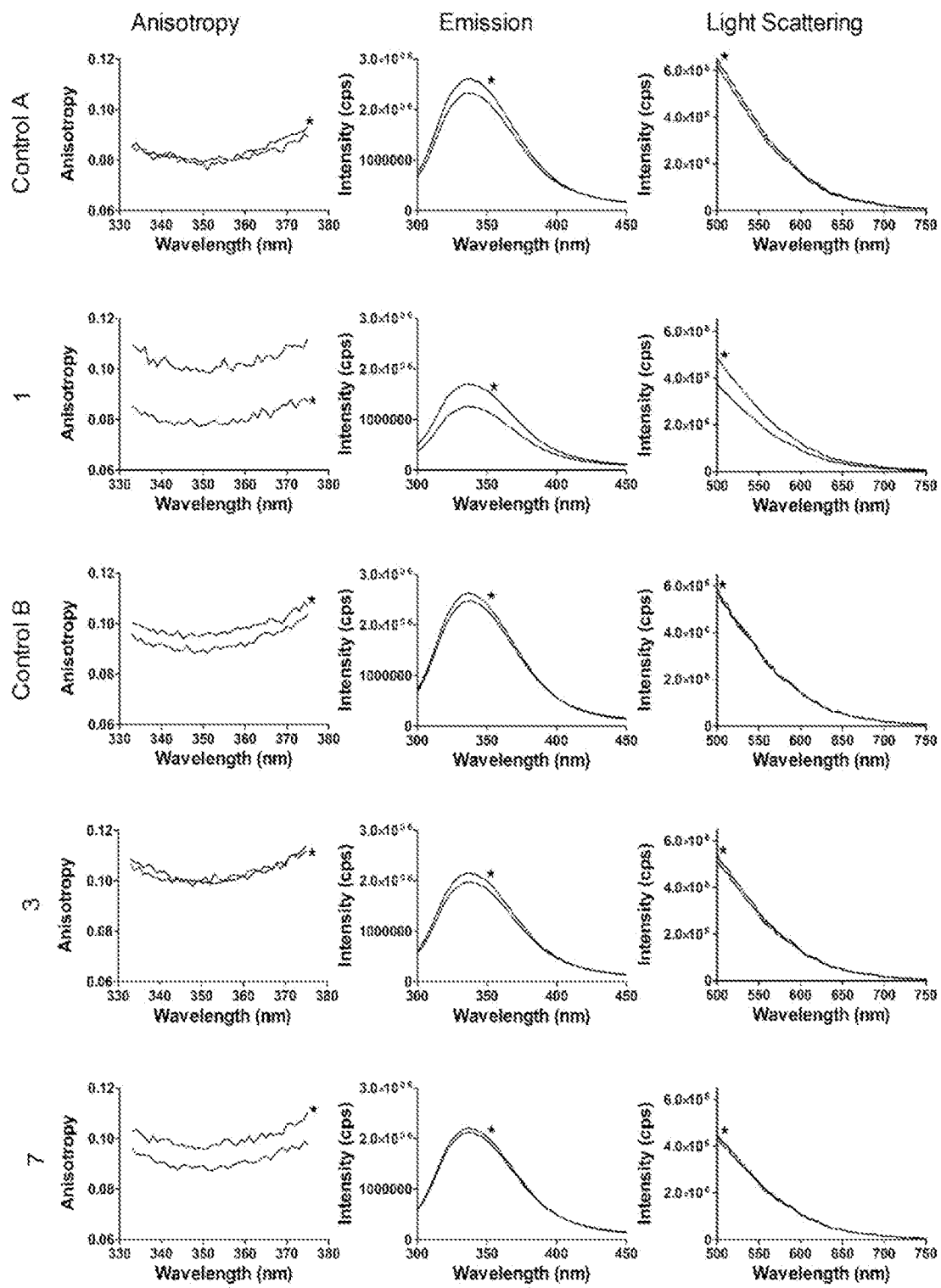

An overview of all the results obtained in this Example is shown in FIG. 4. Each graph represents the results obtained per formulation at different pH. Each column of graphs shows the measurements obtained with a separate assay.

Overall it can be concluded from the turbidity results that Na$_2$SO$_4$-containing formulations seem to have undergone the least change in all the four formulations (B1-4). MgCl$_2$ formulations (C1-4) perform less than Na$_2$SO$_4$ formulations with respect to turbidity, followed by the NaCl containing formulations (D1-4). The results obtained by the DLS, providing additional information on the colloidal properties, showed again a dominant beneficial effect of Na$_2$SO$_4$ on the stability of the MVA-BN-FILO, which was observed for all tested pH values. A particularly large and undesired increase in Z-average diameter after stress was observed for MgCl$_2$ formulations (C1-4), indicating a negative effect of Mg$^{2+}$ ions in chloride containing salt formulations on the colloidal stability of the MVA-BN-FILO. Hence, it can be concluded that the stabilizing effect of the Na$_2$SO$_4$ containing formulations is more robust than the other tested formulations.

Example 5

Experimental Design and Methodology

In this experiment promising formulations from earlier studies as well as novel formulations and a control formulation, which does not contain sulfate, were prepared. An overview of these formulations is shown in Table 4.

Each formulation was subjected to an accelerated stress condition (i.e. 2 weeks at 25° C.; 2W25C). Formulations 5, 6 and 8 were additionally exposed to another accelerated stress condition, namely 1 day at 37° C. (1D37C). The samples were measured for potency before and after applying accelerated stress. Potency measurements were performed by Fluorescence Activated Cell Sorter (FACS) assay, as described below and expressed as relative potency difference (see Table 5).

TABLE 4

Composition of the tested formulations

| | Composition |
|---|---|
| Control formulation | 10 mM Tris pH 7.7 + 140 mM NaCl |
| Formulation 1 | 10 mM Tris pH 8 + 100 mM Na$_2$SO$_4$ |
| Formulation 2 | 10 mM Tris pH 8 + 100 mM Na$_2$SO$_4$ + 6% sucrose |
| Formulation 3 | 10 mM Tris pH 8 + 100 mM Na$_2$SO$_4$ + 5% glycerol |
| Formulation 4 | 10 mM Tris pH 7.7 + 50 mM Na$_2$SO$_4$ + 70 mM NaCl |
| Formulation 5 | 10 mM phosphate pH 7 + 100 mM Na$_2$SO$_4$ |
| Formulation 6 | 10 mM phosphate pH 7 + 100 mM Na$_2$SO$_4$ + 6% sucrose |
| Formulation 7 | 10 mM phosphate pH 7.5 + 100 mM Na$_2$SO$_4$ |
| Formulation 8 | 10 mM phosphate pH 7 + 100 mM Na$_2$SO$_4$ + 5% glycerol |
| Formulation 9 | 10 mM phosphate pH 7 + 50 mM Na$_2$SO$_4$ + 70 mM NaCl |
| Formulation 10 | 10 mM phosphate pH 7 + 50 mM Na$_2$SO$_4$ + 70 mM NaCl + 5% glycerol |
| Formulation 11 | 10 mM phosphate pH 7 + 50 mM Na$_2$SO$_4$ + 5% glycerol |

Results and Conclusion

An overview of the losses in potency as a result of the accelerated stress conditions is shown for each tested formulation in Table 5.

TABLE 5

Overview of the potency analysis results

| Formulations | Buffer | pH | Salt (mM) | Sugar | T0 Potency ($10^8$ IU/mL) | Potency ($10^8$ IU/mL) after 2W25C | Loss in potency after stress (%) |
|---|---|---|---|---|---|---|---|
| Control | Tris | 7.7 | 140 mM NaCl | | 1.01 ± 0.07 | 0.27 ± 0.05 | 73.0 |
| 1 | Tris | 8 | 100 mM $Na_2SO_4$ | | 1.95 ± 0.11 | 1.24 ± 0.03 | 37.0 |
| 2 | Tris | 8 | 100 mM $Na_2SO_4$ | 6% sucrose | 1.83 ± 0.05 | 1.11 ± 0.09 | 39.0 |
| 3 | Tris | 8 | 100 mM $Na_2SO_4$ | 5% glycerol | 1.82 ± 0.08 | 1.16 ± 0.04 | 36.0 |
| 4 | Tris | 7.7 | 70 mM NaCl + 50 mM $Na_2SO_4$ | | 1.84 ± 0.06 | 1.10 ± 0.10 | 40.0 |
| 5 | Phosphate | 7 | 100 mM $Na_2SO_4$ | | 1.18 ± 0.15 | 0.42 ± 0.08 | 64.4 |
| 6 | Phosphate | 7 | 100 mM $Na_2SO_4$ | 6% sucrose | 1.13 ± 0.18 | 0.39 ± 0.06 | 65.5 |
| 7 | Phosphate | 7.5 | 100 mM $Na_2SO_4$ | | 1.39 ± 0.17 | 0.69 ± 0.11 | 50.4 |
| 8 | Phosphate | 7 | 100 mM $Na_2SO_4$ | 5% glycerol | 1.12 ± 0.26 | 0.41 ± 0.06 | 63.4 |
| 9 | Phosphate | 7 | 70 mM NaCl + 50 mM $Na_2SO_4$ | | 1.14 ± 0.09 | 0.38 ± 0.05 | 66.7 |
| 10 | Phosphate | 7 | 70 mM NaCl + 50 mM $Na_2SO_4$ | 5% glycerol | 1.36 ± 0.18 | 0.47 ± 0.06 | 65.4 |
| 11 | Phosphate | | 50 mM $Na_2SO_4$ | 5% glycerol | 1.35 ± 0.13 | 0.37 ± 0.01 | 72.6 |

| Formulations | Buffer | pH | Salt (mM) | Sugar | T0 Potency ($10^8$ IU/mL) | T0 Potency ($10^8$ U/mL) After 1D37C | Loss in potency after stress (%) |
|---|---|---|---|---|---|---|---|
| 5 | Phosphate | 7 | 100 mM $Na_2SO_4$ | | 1.18 ± 0.15 | 0.55 ± 0.10 | 53.4 |
| 6 | Phosphate | 7 | 100 mM $Na_2SO_4$ | 6% sucrose | 1.13 ± 0.18 | 0.52 ± 0.11 | 54.0 |
| 8 | Phosphate | 7 | 100 mM $Na_2SO_4$ | 5% glycerol | 1.12 ± 0.26 | 0.61 ± 0.06 | 45.5 |

Overall, the results indicate that the presence of sulfate in the tested compositions has a positive effect on the potency loss, following accelerated stress. Moreover, the combination of sulfate and a relatively higher pH (>7.5) further improves stability (see formulations 1, 2, 3, 4 and 7). In addition, the presence of glycerol in the formulations seemed to also reduce the loss in potency. This is evidenced by the potency loss observed for formulations 3 and 8 (specifically after 1D37C for formulation 8).

Example 6

Experimental Design and Methodology

In this experiment promising sulfate containing formulations from earlier studies (Example 5, Table 5: formulations 1, 3 and 7) as well as control formulations without sulfate were prepared. MVA-BN-FILO drug substance has been buffer-exchanged using ultrafiltration/dia-filtration. The formulations, around the desired drug product concentration, were filled into glass vials, stoppered and capped. An overview of the formulations is shown in Table 6. Each formulation was subjected to the following stress conditions: i) 3 months at 5° C., ii) 3 months at −20° C., iii) 20 freeze-thaw cycles, iv) agitation for 1 day at 200 rpm. The samples were measured before and after one of the indicated stress conditions, by various spectroscopic methods (e.g. anisotropy, intrinsic fluorescence, 90 degrees light-scattering, phosphorescence, dynamic light-scatter and turbidity). In addition, the samples were measured for potency.

Measurements of the turbidity were performed on a BioTek Neo plate reader. Dynamic light scattering (DLS) (noted as Z-average diameter change and PDI change) measurements were performed on the Zetasizer. Measurements of the anisotropy, intrinsic fluorescence, 90 degrees light-scattering and phosphorescence were performed in quartz cuvettes on a Fluoromax 4 spectrofluorometer (Jobin Yvon Horiba, UK). Potency measurements were performed by Fluorescence Activated Cell Sorter (FACS) assay and expressed as Infectious Units per mL (Table 7), as well as relative potency difference (Table 8).

TABLE 6

Composition of the tested formulations

| Formulation | Composition |
|---|---|
| Control A | 10 mM Tris pH 7.7 + 140 mM NaCl |
| Control B | 10 mM Tris pH 7.7 + 70 mM NaCl + 5% glycerol |
| 1 | 10 mM Tris pH 8.0 + 100 mM $Na_2SO_4$ |
| 3 | 10 mM Tris pH 8.0 + 100 mM $Na_2SO_4$ + 5% glycerol |
| 7 | 10 mM Na/K phosphate pH 7.5 + 100 mM $Na_2SO_4$ |

Results and Conclusion

Figure 9:
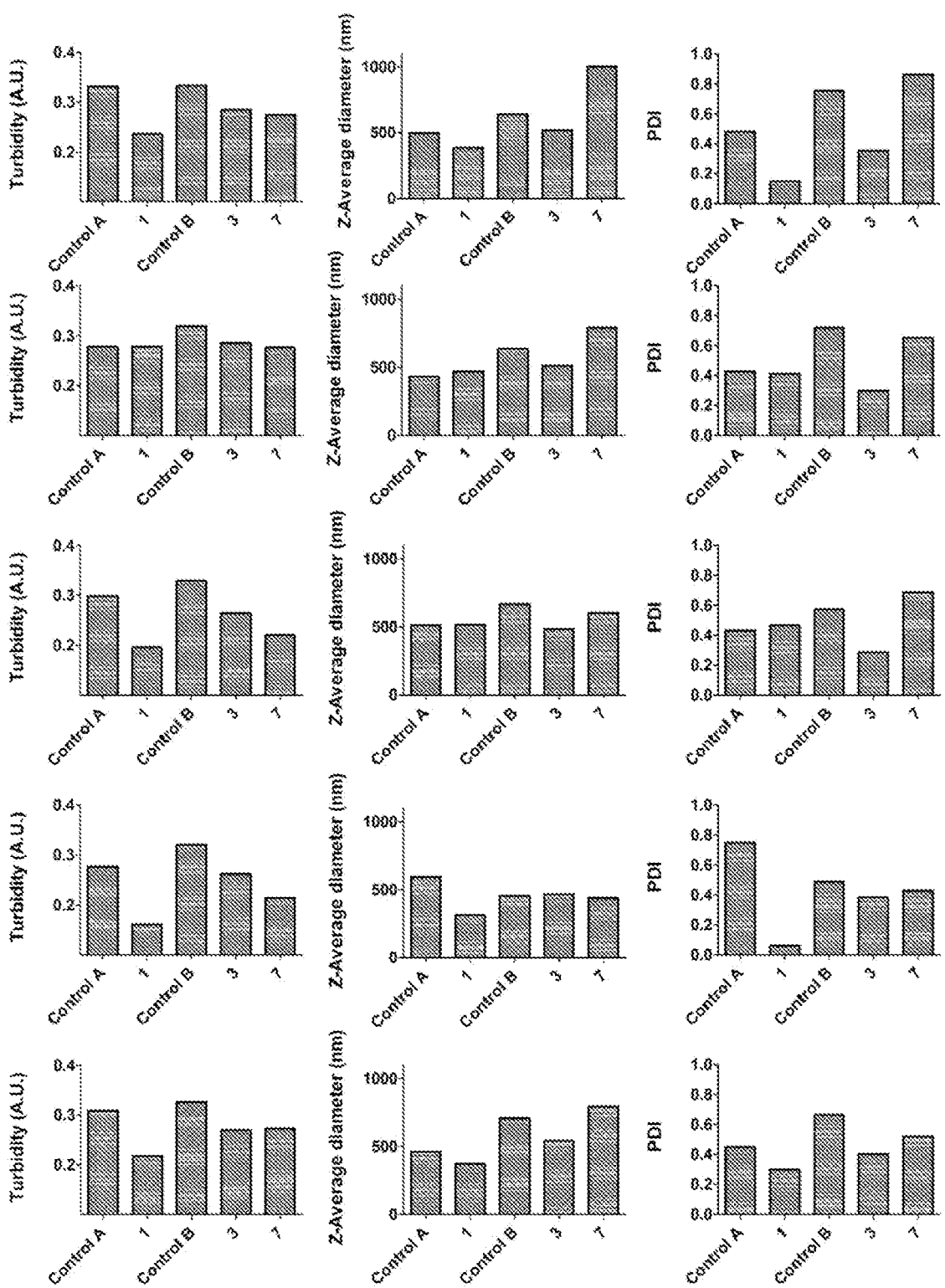

The potency of the formulations before and after applying the stress conditions is presented in Tables 7 and 8. FIGS. 5, 6, 7 and 8 contain the anisotropy, fluorescence emission and 90 degrees light scattering spectra for the MVA formulations after preparation and after the subjected stress condition of 3 months at 5° C., 3 months at −20° C., 20 freeze-thaw cycles and 1 day agitation at 200 rpm, respectively. FIG. 9 contains the turbidity, Z-average diameter and PDI of the tested samples. Formulation 3 showed no potency loss after 3 months at −20° C., after 20 freeze-thaw cycles and after 1 day agitation (tables 7 and 8). The measured variations were within the assay variation. Formulation 7 showed no potency loss after 1 day agitation, whereas there was a strong decrease after 3 months at −20° C., or 20 freeze-thaw cycles (Tables 7 and 8).

The MVA formulations are an inherent combination of the infectious MVA particles (active substance) as well as various host cell proteins and other process derived impurities; all together it forms a whitish suspension that contains small and large particles with sizes measured by average diameter and PDI. Turbidity and 90 degrees light scatter provide additional insight in the particulate nature of these suspensions. In general, it can be concluded that sulfate in the formulations resulted in reduction of turbidity, which is most pronounced for Formulation 1 (FIG. 9). In this example, upon the indicated stress conditions, the disruptive effect of sulfate on reducing the larger particles in Formulation 1 was further increased compared to Control A, as measured by even lower values of turbidity, light-scatter, Z-average and PDI (FIGS. 5-9).

Formulation 3, MVA in Tris with sodium sulfate and glycerol, showed no or minimal change in anisotropy spectra, fluorescence emission spectra, 90 degrees light-scattering, turbidity, Z-average diameter and PDI after the following stress conditions: i) 3 months at −20° C. ii) 20 freeze-thaw cycles and iii) agitation for 1 day at 200 rpm (FIGS. 6-9). This is in agreement with the observation of no change in potency loss (within assay variation). The sulfate in combination with Tris and glycerol impacted the MVA formulations positively and a proper equilibrium was established regarding the particulate nature and colloidal properties of the suspension; e.g. the formulation maintained, when compared to T0, its turbidity as well as some heterogeneity as shown by the PDI around 0.3 (FIG. 9).

Formulation 7, MVA in phosphate buffer with sodium sulfate, had high PdI and high Z-average values (FIG. 9) which indicates the presence of many small and large particles. Formulation 7 stabilized the MVA against agitation induced stress in a similar way as Formulation 3. Agitation did not induce a change in fluorescence emission, 90 degrees light-scattering or turbidity of Formulation 7, although a small drop in anisotropy values were measured. This indicates that on average the Trp environment became less rigid (e.g. dissociation or unfolding) without impacting the overall particulate nature of the MVA colloidal suspension. Agitation did not induce a change in potency of Formulation 7; the changes observed were likely caused by dissociation or degradation of non-MVA related proteins. In addition, the PdI and Z-average values of Formulation 7 after agitation for 1 day were lower compared to values after 3 months at 5° C., or 3 months at −20° C. indicative that the particles and its size distribution were more in line with what is expected from purified MVA particles without a large extent of aggregates or clusters. Formulation 7 compared to Formulation 1 indicates that the presence of phosphate in combination with sulfate is more protective against agitation induced stress than Tris with sulfate (Tables 7 and 8).

In this example, Control Formulations B (Tris, glycerol and NaCl) had a potency loss similar or worse compared to the Control Formulation A (Tris and NaCl), indicating that the presence of glycerol did not improve the physical and biological properties of the Control formulation not containing sulfate. However, when replacing the sodium chloride of Control Formulation B with sodium sulfate (Formulation 3) a stabilization of the MVA formulation resulted with minimal to no change in potency; the values presented in Tables 7 and 8 for the −20° C., 20× freeze-thawing and agitation conditions, are within the assay variation.

In conclusion, the potency and physical stability of MVA was stabilized by addition of sulfate salts to the formulation. Combination of sulfate with glycerol stabilized the MVA particle in both frozen state and upon freeze-thawing. The improved MVA stability can be beneficial for supply chain, including long term storage, stockpiling and use in the field.

TABLE 7

Potency of the formulations at T0 and after stress condition

| | Potency ($10^8$ IU/mL) | | | | |
|---|---|---|---|---|---|
| Formulation | T0 | 3M5C | 3M-20C | 20xFT | Agitation |
| Control A | 2.97 ± 0.27 | 2.11 ± 0.56 | 1.93 ± 0.58 | 1.80 ± 0.51 | 1.98 ± 0.39 |
| Control B | 3.10 ± 0.32 | 1.26 ± 0.17 | 2.08 ± 0.58 | 2.09 ± 0.35 | 2.18 ± 0.60 |
| 1 | 2.80 ± 0.33 | 1.42 ± 0.01 | 1.56 ± 0.36 | 1.53 ± 0.42 | 2.07 ± 0.46 |
| 3 | 3.91 ± 0.83 | 2.81 ± 0.11 | 4.25 ± 0.46 | 4.32 ± 0.34 | 3.54 ± 0.65 |
| 7 | 2.79 ± 0.16 | 1.75 ± 0.21 | 0.95 ± 0.15 | 1.07 ± 0.13 | 3.04 ± 0.52 |

TABLE 8

Relative loss of potency (%) after stress of the tested formulations compared to potency at T0 (=100%)

| | Loss in potency after stress (%) | | | |
|---|---|---|---|---|
| Formulation | 3M5C | 3M-20C | 20xFT | Agitation |
| Control A | 29 | 35 | 39 | 33 |
| Control B | 59 | 33 | 33 | 30 |
| 1 | 49 | 44 | 45 | 26 |
| 3 | 28 | −9 | −10 | 9 |
| 7 | 37 | 66 | 62 | −9 |

Methods Used to Determine the Stability
Intrinsic Fluorescence Assay

MVA proteins contain aromatic amino acids (fluorophores) that reemit light after excitation, in particular tryptophan and to a lesser extent tyrosine and phenylalanine. The emission maximum and quantum yield of tryptophan depend strongly on the polarity of its environment. In a polar, aqueous environment (e.g. the surface of a globular protein, or in a dissociated and free state) the quantum yield is relatively low, while in a polar environment (e.g. the inside of an aggregate, or within a lipophilic viral envelope) the quantum yield increases. This feature makes tryptophan fluorescence a useful tool for studying protein conformational change, aggregation, degradation, dissociation, and molecular interactions.

The fluorescence intensity is known in the art to be a sensitive measure of protein stability. Either an increase or a decrease may be observed upon stress, depending on the nature of the changes occurring in the sample. Protein unfolding and capsid dissociation is expected to lead to a decrease in intrinsic fluorescence, and aggregation is expected to lead to an increase. Changes in the position of the emission maximum provide additional information on the environment of the fluorophore. In general, a red shift (shift of intensity maximum towards longer wavelengths) occurs in case of exposure of the fluorophores to a more aqueous environment. When the fluorophores are more shielded from water, a blue shift (shift of intensity maximum to lower wavelengths) typically occurs.

The obtained fluorescence for stressed samples should always be compared to the control samples. A change (higher or lower) compared to the t=0 samples is indicative of a less stable formulation. Stressed samples remaining close to the t=) sample values are more stable.

Two different fluorescence techniques were applied, cuvette based spectrofluorometer and a microplate based plate reader. The precision of both techniques is <5% (CV %) in the range used.

The cuvette based steady-state fluorescence measurements were performed with a Fluoromax-4 spectrofluorometer (Jobin Yvon Horiba, UK). The measurements were made at 25° C. using a thermostated cuvette holder. Hellma quartz cuvettes were used. The samples were excited at 290 nm and the emission was monitored between 300 nm and 450 nm using bandpasses of 2 nm (excitation) and 4 nm (emission) and integration time of 0.1 for the steady-state emission measurements.

Microplate based intrinsic fluorescence assay were measured with a Biotek Neo 2 plate reader. Samples are transferred in triplicate to a UV-transparent, flat-bottom microplate. Tryptophan fluorescence is measured after excitation at 280 nm and a bandwidth of 10 nm, and an emission between 310 nm to 450 nm.

Anisotropy

Steady-state fluorescence anisotropy measures the ability of fluorophores to turn polarized light. An excitation wavelength is polarized in one direction and subsequently turned when emitted by the fluorophore. A filter is used to measure emission wavelength in the same plane as the excited wavelength, which means that only light in the same plane as the excitation wavelength will be detected. The more the polarized light is turned, the lower the signal on the detector. The ability to turn light depends on the average flexibility of the individual fluorophores; the more flexible the fluorophore is, the more the light will be turned and the lower the signal on the detector. This makes anisotropy a useful tool for studying protein conformational change, aggregation, degradation, dissociation and molecular interactions.

Anisotropy is known in the art to be a sensitive measure of protein stability. Either an increase or a decrease may be observed upon stress, depending on the nature of the changes occurring in the sample. Protein unfolding and capsid dissociation is expected to lead to a decrease in anisotropy, and aggregation is expected to lead to an increase. The obtained anisotropy for stressed samples should always be compared to the control samples. Since an increase or decrease after applied stress is dependent on the degradation pathway and specific for each Active Pharmaceutical Ingredient (API), it cannot be predicted. A change (higher or lower) compared to the t=0 samples is indicative of a less stable formulation. Stressed samples remaining close to the t=0 sample values are more stable.

Steady-state fluorescence anisotropy measurements were performed with a Fluoromax-4-spectrofluorometer (Jobin Yvon Horiba, UK). The measurements were made at 25° C. using a thermostated cuvette holder. Hellma quartz cuvettes were used. The steady-state anisotropy measurements were performed using a T-format configuration with Glan-Thompson prism polarizers. The anisotropy was measured in the emission peak range (333-375 nm) resulting from excitation at 290 nm. The fluorescence anisotropy, A, was calculated from the equation:

$$A = \frac{I_{0,0} - G \times I_{0,90}}{I_{0,0} + 2G \times I_{0,90}}$$

where G is a correction factor, $G=I_{90,0}/I_{90,90}$. $I_{m,n}$ is the fluorescence intensity at a given wavelength and the subscripts refer to the position of polarizers in the excitation (m) and the emission (n) beams relative to the vertical axis. The spectra were recorded with a 1.0 s integration time per 1 nm spectrum step.

90 Degrees Light Scattering

The cuvette based 90 degrees light scattering measurements were performed with a Fluoromax-4 spectrofluorometer (Jobin Yvon Horiba, UK). The measurements were made at 25° C. using a thermostated cuvette holder. Hellma quartz cuvettes were used. The light scatter at a 90 degrees angle was measured at wavelengths between 500 and 750 nm, by monitoring the emission at the wavelengths of excitation using optimized bandpass combinations and integration time of 0.01 s. The light scatter spectra provide information on the concentration, refractive index and size of the particles in solution. This technique has been shown to be sensitive to small changes in aggregation state of biological formulations. For example, a decrease in light-scatter can be explained by either a reduction in concentration of particles or a reduction in size of the same number of particles, or a combination thereof. An increase in light-scatter is often associated with aggregation due to an increase in number of particles or an increase in the size of the same number of particles, or a combination thereof.

Dynamic Light Scattering

Dynamic Light Scattering (DLS) is a technique that is used to measure the size distribution of particles in suspension or in solution. Polarized laser light is entered into a sample and is scattered by particles present in the sample. The scatter light is subsequently collected by a photomultiplier. Here the fluctuations of the intensity through time are analyzed. Since smaller particles travel through the solution faster than larger particles, due to their higher Brownian motion, the fluctuations in intensity of smaller particles is higher. Since MVA is a particle and scatters polarized laser light, DLS can be used to determine the increase (e.g. aggregation) and/or decrease (e.g. dissociation) of the size of MVA particles, which makes DLS a useful technique for detection aggregation or dissociation.

In DLS, samples were transferred in triplicate to a UV-transparent, flat-bottom microplate. The particle size and distribution were measured using DLS equipment Zetasizer APS (Malvern, UK), equipped with 10 mV He—Ne laser (830 nm) and operated at an angle of 90°.

The obtained size distribution for stressed samples was compared to the control samples. A change (higher or lower) compared to the t=0 samples is indicative of a less stable formulation. Stressed samples remaining close to the t=0 sample values are more stable.

Turbidity Measurements at 350 nm

Turbidimetry measures the loss of intensity of transmitted light due to scattering of particles in samples (apparent absorbance), detected at a wavelength where the molecules in the sample do not absorb light (e.g. 350 nm for samples in which proteins are the main chromophore). When molecules aggregate or form supramolecular complexes, the light scattering, which was random when coming from the separate particles, now becomes coherent, and thereby the measured intensity increases. This makes light scattering and turbidimetry useful techniques for detecting aggregation and complex formation or dissociation.

In the turbidity assay, samples are transferred in triplicate to a UV-transparent, flat-bottom microplate. Absorbance spectra are recorded by a microplate reader between 230 and 500 nm, and the absorbance at 975 nm is measured to determine and possibly correct for differences in optical path length. Control samples consisting of the formulations without MVA were included in the assay to correct for scattering or absorbing matrix components if required. The apparent absorbance at 350 nm was used as a quantitative measure for turbidity.

The turbidity assay is stability-indicating for MVA samples. MVA aggregation leads to an increase in turbidity and capsid dissociation to a decrease. The assay precision is <5% (CV %) at turbidity values >1 NTU.

The obtained turbidity for stressed samples should always be compared to the control samples. A change (higher or lower) compared to the t=0 samples is indicative of a less stable formulation. Stressed samples comparable to the t=0 samples are expected to be more stable.

Phosphorescence

Phosphorescence refers to emission from the excited triplet state, whereas fluorescence refers to the emission from the excited singlet state. Phosphorescence is basically the emission of radiation in a similar manner to fluorescence (ns scale) but on a longer timescale (ms to ms), so that emission continues after excitation ceases. According to the Jablonski diagram, the fluorophore absorbs light and goes from the ground state to the singlet state, followed by an intersystem crossing to the triplet state. The emission from the triplet state (phosphorescence) is at a lower energy and thus at a higher wavelength compared to the fluorescence. Phosphorescent signal can be a specific property of an Active Pharmaceutical Ingredient (API), and in case of a decrease provide an indication of conformational change, degradation or dissociation. An increase in phosphorescence emission can occur when larger and rigid structures are formed, e.g. in case of protein aggregation.

The phosphorescence measurements were performed with a Fluoromax-4 spectrofluorometer (Jobin Yvon Horiba. UK). The measurements were made at 25° C. using a thermostated cuvette holder. Hellma quartz cuvettes were used. The samples were excited at 343 nm and the phosphorescence was monitored between 360 nm and 550 nm using bandpasses of 2 nm (excitation) and 4 nm (emission) and an integration time of 0.5 S.

Methods to Determine the Infectivity (Potency)

Fluorescence Activated Cell Sorter (FACS) Assay

The titer (InfU/mL) of recombinant or non-recombinant MVA was determined by a Fluorescence Activated Cell Sorter (FACS) assay. MVA infected Baby Hamster Kidney Cells 21 (BHK-21) cells were immune-stained with a fluorochrome-conjugated antibody specific for vaccinia virus (VACV) which were subsequently acquired and quantified using the FACSVerse™ (BD Bioscience) instrument equipped with a BD Flow Sensor for quantitative cell counting.

In more detail, $2.5 \times 10^5$ BHK 21 cells (source ATCC) were seeded in GMEM/9% FBS/1.8% Ala-Gln into 12 well plates. Cells were infected on the following day with a serial dilution of the MVA virus stock of interest. Following 1 h of incubation at 37 degrees Rifampin (100 μg/mL in GMEM/9% FBS/1.8% Ala-Gln) was added. Cells were harvested 19±2 h after infection and fixed and permeabilized with the BD Perm/Wash™ kit prior to antibody staining. Fixed cells were incubated with anti-vaccinia FITC (Fitzgerald Industries International, Cat #60-v68) for 60-90 minutes. Then, the percentage of virus-positive cells was determined by flow cytometry using the BD FACSVerse™ cytometer. The total cell count was determined by using the BD FACSVerse™ Flow Sensor on unstained cells that were fixed in parallel. The calculation of InfU/mL of the assay was based on the percentage of virus-positive cells, the virus dilution used during infection, the infection volume and the average cell number per well. To limit the effect of cell count well to well variability, the cell number was established by averaging the cell count of multiple wells. For calculation of the InfU/mL of the virus sample, only dilutions containing 2 to 35% VACV-positive cells were included. The calculation of the InfU/mL per sample dilution was done according to the following formulas:

$$Inf. \ U/\text{ml} = \text{average cell number} * \left[-LN\left(1 - \frac{\% \ VACV \ pos. \ \text{cells}}{100}\right)\right] * \frac{\text{virus dilution}}{\text{infection volume}}$$

Tissue Culture Infectious Dose 50 ($TCID_{50}$) MVA Infectivity Assay

The $TCID_{50}$ is a method for titrating the infectivity of MVA, using 10-fold dilutions in a 96-well format as described in Example 2 of WO 03/053463. The titration of MVA was performed in a $TCID_{50}$-based assay using 10-fold dilutions in a 96-well format. At the endpoint of the assay, infected cells were visualized using an anti-vaccinia virus antibody and an appropriate staining solution. 2-3 day old primary CEF (chicken embryo fibroblasts) cells were diluted to $1 \times 10^5$ cells/mL in 7% RPMI. 10 fold dilutions were done with 8 replicates per dilution. Following dilution, 100 μL were seeded per well of 96-well plates. Cells were then incubated over night at 37° C., and 5% $CO_2$.

Dilutions of the virus containing solutions were made in 10-fold steps using RPMI without fetal calf serum. Then, 100 μL of every virus sample was added to the cell containing wells. The 96-well-plates were incubated at 37 degrees centigrade with 5% $CO_2$ for 5 days to allow infection and viral replication. Cells were stained 5 days after infection with a vaccinia virus specific antibody. For the detection of the specific antibody, a horseradish peroxidase (HRP) coupled secondary antibody was used. The MVA specific antibody was an anti-vaccinia virus antibody, rabbit polyclonal, IgG fraction (Quartett, Berlin, Germany #9503-2057). The secondary antibody was anti-rabbit IgG antibody, HRP coupled goat polyclonal (Promega, Mannheim. Germany, #W4011). The color reaction was carried out according to known techniques. Every well with cells that were positive in the color reaction were marked as positive for the calculation of the $TCID_{50}$. The titer was calculated by using the Spearman-Kaerber method of calculation. The data can also be represented as a log of virus titer which is the relative difference for any given time-point from T=0 time-point.

The examples as described above are considered as exemplary only, with a true scope and spirit of the invention being indicated by the following claims.

The invention claimed is:

1. A composition comprising a) a poxvirus; b) a buffer; and c) a sulfate salt at a concentration between about 5 mM and 300 mM, wherein said composition has a pH of between about 6.0 and 8.5.

2. The composition of claim 1, wherein the poxvirus is a vaccinia virus or a modified vaccinia Ankara (MVA) virus.

3. The composition of claim 1, wherein the poxvirus is a recombinant poxvirus.

4. The composition of claim 2, wherein the MVA is a recombinant MVA expressing a filovirus protein, or one, two, or three filovirus glycoproteins.

5. The composition of claim 1, wherein the virus titer is in the range of about $1\times10^7$ InfU/mL to about $2\times10^9$ InfU/mL, about $1\times10^7$ InfU/mL to about $4\times10^8$ InfU/mL, or about $0.1\times10^8$ InfU/mL to about $4\times10^8$ InfU/mL.

6. The composition of claim 1, wherein the composition is a liquid composition or liquid frozen.

7. The composition of claim 1, wherein the buffer is a Tris buffer, a phosphate buffer, a citrate buffer or a citrate/phosphate buffer at a concentration of about 5 to about 40 mM, or about 5 to about 25 mM.

8. The composition of claim 1, wherein the buffer is a Tris buffer at a pH of about 6.5 to about 8.5, a pH of about 7.5 to about 8.5, or a pH of about 8; or wherein the buffer is a phosphate buffer at a pH of about 6.5 to about 8.5, a pH of about 6.8 to about 7.8, or a pH of about 7.0 to about 7.5.

9. The composition of claim 1, wherein the sulfate salt is selected from the group consisting of sodium sulfate, potassium sulfate, magnesium sulfate, ammonium sulfate, and a combination thereof.

10. The composition of claim 1, wherein the sulfate salt concentration is from about 5 mM to about 150 mM.

11. The composition of claim 1, wherein the buffer is a Tris buffer at a concentration of about 10 mM, the sulfate salt is sodium sulfate at a concentration of about 100 mM, and wherein said composition has a pH of about 8; or wherein the buffer is a phosphate buffer at a concentration of about 10 mM, the sulfate salt is sodium sulfate at a concentration of about 100 mM, and wherein said composition has a pH of about 7.5.

12. The composition of claim 1, further comprising sodium chloride at a concentration of about 10 mM to about 100 mM.

13. The composition of claim 1, further comprising a sugar, a sugar alcohol and/or a polyol.

14. The composition of claim 13, wherein the polyol is glycerol at a concentration of about 1% (w/w) to about 6% (w/w).

15. The composition of claim 14, wherein the glycerol concentration is about 5% (w/w).

16. The composition of claim 13, wherein the sugar is sucrose at a concentration of about 1% (w/w) to about 10% (w/w).

17. A pharmaceutical composition comprising the composition of claim 1.

18. A method of preparing the composition of claim 1, comprising combining a) the poxvirus; b) the buffer; and c) the sulfate salt at a concentration of about 5 mM to about 300 mM, wherein said composition has a pH of about 6.0 to about 8.5.

19. A method of stabilizing a poxvirus composition comprising preparing the composition of claim 1 comprising the poxvirus.

20. The method of claim 19, further comprising storing the composition at a temperature from 2 degrees centigrade to 8 degrees centigrade.

* * * * *